(12) United States Patent
McNeel et al.

(10) Patent No.: US 10,111,940 B2
(45) Date of Patent: Oct. 30, 2018

(54) PROSTATE CANCER VACCINE

(71) Applicant: WISCONSIN ALUMNI RESEARCH FOUNDATION, Madison, WI (US)

(72) Inventors: Douglas G. McNeel, Madison, WI (US); Brian M. Olson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 127 days.

(21) Appl. No.: 15/238,016

(22) Filed: Aug. 16, 2016

(65) Prior Publication Data

US 2017/0014498 A1    Jan. 19, 2017

Related U.S. Application Data

(60) Continuation of application No. 14/614,137, filed on Feb. 4, 2015, now Pat. No. 9,433,668, which is a continuation of application No. 13/968,854, filed on Aug. 16, 2013, now Pat. No. 8,962,590, which is a continuation of application No. 13/031,396, filed on Feb. 21, 2011, now Pat. No. 8,513,210, which is a division of application No. 11/848,607, filed on Aug. 31, 2007, now Pat. No. 7,910,565.

(60) Provisional application No. 60/841,769, filed on Sep. 1, 2006.

(51) Int. Cl.
| | |
|---|---|
| *A61K 39/00* | (2006.01) |
| *A61K 31/70* | (2006.01) |
| *G01N 33/569* | (2006.01) |
| *G01N 33/574* | (2006.01) |
| *A61K 38/19* | (2006.01) |

(52) U.S. Cl.
CPC .......... *A61K 39/0011* (2013.01); *A61K 31/70* (2013.01); *A61K 38/193* (2013.01); *G01N 33/56972* (2013.01); *G01N 33/57434* (2013.01); *A61K 2039/53* (2013.01); *A61K 2039/55516* (2013.01); *A61K 2039/585* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,548,064 B1 | 4/2003 | Tureci et al. |
| 6,562,798 B1 | 5/2003 | Schwartz |
| 6,800,730 B1 | 10/2004 | Tureci et al. |
| 6,821,767 B1 | 11/2004 | French et al. |
| 7,129,078 B2 | 10/2006 | French et al. |
| 7,179,797 B2 | 2/2007 | McNeel |
| 7,223,741 B2 | 5/2007 | Krieg |
| 7,238,778 B2 | 7/2007 | Apolito et al. |
| 7,910,565 B2 | 3/2011 | McNeel et al. |
| 8,513,210 B2 | 8/2013 | McNeel et al. |
| 2004/0142890 A1 | 7/2004 | McNeel |

OTHER PUBLICATIONS

Acsadi, et al., Direct Gene Transfer and Expression into Rat Heart In Vivo, The New Biologist, 1991, 3(1):71-81.
Ayyoub, et al., Identification of an SSX-2 Epitope Presented by Dendritic Cells to Circulating Autologous CD4+ T Cells, Journal of Immunology, 2004, 172:7206-7211.
Budker, et al., Naked DNA Delivered Intraportally Expresses Efficiently in Hepatocytes, Gene Therapy, 1996, 3:593-598.
Budker, et al., pH-Sensitive, Cationic Liposomes: A New Synthetic Virus-Like Vector, Nature Biotechnolgoy, 1996, 14:760-764.
Budker, et al., The Efficient Expression of Intravascularly Delivered DNA in Rat Muscle, Gene Therapy, 1998, 5:272-276.
Chang, et al., Fusion Proteins Containing Androgen Receptor Sequences and Their Use in the Production of Poly- and Monoclonal Anti-Androgen Receptor Antibodies, Endocrinology, 1989, 123(2):1097-1099.
Chen, et al., Molecular Determinants of Resistance to Antiandrogen Therapy, Nature Medicine, 2004, 10:33-39.
Chen, et al., Induction of CD8+ T Cell Responses to Dominant and Subdominant Epitopes and Protective Immunity to Sendai Virus Infection by DNA Vaccination, Journal of Immunology, 1998, 160:2425-2432.
Chichet, et al., Androgen Receptor Distribution, PAS and Alcyan Blue Reaction in the Vomeronasal Organ and the Nasal Septum Mucosa of the Developing Male Rat, Int. J. Morphol., 2007, 25(3):579-585.
Cho, et al., Immunostimulatory DNA-Based Vaccines Induce Cytotoxic Lymphocyte Activity by a T-Helper Cell-Independent Mechanism, Nature Biotechnology, 2000, 18:509-514.
Costaglioila, et al., Genetic Immunization Against the Human Thyrotropin Receptor Causes Thyroiditis and Allows Production of Monoclonal Antibodies Recognizing the Native Receptor, Journal of Immunology, 1998, 160:1458-1465.
Danko, et al., Pharmacological Enhancement of In Vivo Foreign Gene Expression in Muscle, Gene Therapy, 1994, 1 (2):114-121.
Davis, et al., Direct Gene Transfer into Skeletal Muscle In Vivo: Factors Affecting Efficiency of Transfer and Stability of Expression, Human Gene Therapy, 1993, 4:151-159.
Eder, et al., Targeting the Androgen Receptor in Hormone-Refractory Prostate Cancer—New Concepts, Future Oncology, 2005, 1(1):93-101.
Hartmann, et al., Delineation of a CpG Phosphorothioate Oligodeoxynucleotide for Activating Primate Immune Responses in Vitro and In Vivo, Journal of Immunology, 2000, 164:1617-1624.
Irvine, et al., The Next Wave of Recombinant and Synthetic Anticancer Vaccines, Cancer Biology, 1995, 6:337-347.
Iwasaki, et al., The Dominant Role of Bone Marrow-Derived Cells in CTL Induction Following Plasmid DNA Immunization at Different Sites, Journal of Immunology, 1997, 159:11-14.

(Continued)

*Primary Examiner* — Qian Janice Li
(74) *Attorney, Agent, or Firm* — Quarles & Brady, LLP

(57) ABSTRACT

Androgen receptor-based vaccines for eliciting an immune reaction in vivo against cells expressing androgen receptor are disclosed. The vaccines are useful in the treatment of prostate cancer. Also disclosed are methods for inducing immune reaction to androgen receptor or treating prostate cancer in a mammal, using the vaccines and pharmaceutical compositions comprising the vaccines.

8 Claims, 15 Drawing Sheets

Specification includes a Sequence Listing.

(56) References Cited

OTHER PUBLICATIONS

Kaczmarczyk, et al., Induction of cre Recombinase Activity Using Modified Androgen Receptor Ligand Binding Domains: A Sensitive Assay for Ligand-Receptor Interactions, Nucleic Acids Research, 2003, 31(15):e86, 8 pages.

Kaplan-Lefko, et al., Pathobiology of Autochthonous Prostate Cancer in a Pre-Clinical Transgenic Mouse Model, The Prostate, 2003, 55:219-237.

Lee, et al., Comparison of Various Expression Plasmids for the Induction of Immune Response by DNA Immunization, Mol. Cells, 1997, 7(4):495-501.

Manthorpe, et al., Gene Therapy by Intramuscular Injection of Plasmid DNA: Studies on Firefly Luciferase Gene Expression in Mice, Human Gene Therapy, 1993, 4:419-431.

Meidenbauer, et al., Direct Visualization of Antigen-Specific T Cells Using Peptide-MHC-Class I Tetrameric Complexes, Methods, 2003, 31:160-171.

Mincheff et al., Naked DNA and Adenoviral Immunizations for Immunotherapy of Prostate Cancer: A Phase I/II . Clinical Trial, European Urology, 2000, 38:208-217.

Olson, et al., Antibody and T-Cell Responses Specific for the Androgen Receptor in Patients With Prostate Cancer, The Prostate, 2007, 67:1729-1739.

Palmowski, et al., The Use of HLA Class I Tetramers to Design a Vaccination Strategy for Melanoma Patients, Immunological Reviews, 2002, 188:155-163.

Prikler, et al., Adaptive Immunotherapy of the Advanced Prostate Cancer—Cancer Testis Antigen (CTA) as Possible Target Antigens, Aktuel Urol., 2004, 35:326-330.

Raz, et al., Intradermal Gene Immunization: The Possible Role of DNA Uptake in the Induction of Cellular Immunity to Viruses, Proc. Natl. Acad. Sci. USA, 1994, 91:9519-9523.

Scanlan, et al., The Cancer/Testis Genes: Review, Standardization, and Commentary, Cancer Immunity, 2004, 4:1, 15 pages.

Scher, et al., Targeting the Androgen Receptor: Improving Outcomes for Castration-Resistant Prostate Cancer, Endocrine-Related Cancer, 2004, 11:459-476.

Suarez-Quian, et al., Androgen Receptor Distribution in Adult Human Testis, Journal of Clinical Endocrinology and Metabolism, 1999, 84(1):350-358.

Thomson, et al., Delivery of Multiple CD8 Cytotoxic T Cell Epitopes by DNA Vaccination, Journal of Immunology, 1998, 160:1717-1723.

Tighe, et al., Gene Vaccination: Plasmid DNA is More Than Just a Blueprint, Immunology Today, 1998, 19(2):89-97.

Tureci, et al., Identification of a Meiosis-Specific Protein as a Member of the Class of Cancer/Testis Antigens, Proc. Natl. Acad. Sci. USA, 1998, 95:5211-5216.

Wagner, et al., Identification of an HLA-A*02 Restricted Immunogenic Peptide Derived from the Cancer Testis Antigen HOM-MEL-40/SSX2, Cancer Immunity, 2003, 3:18, 15 pages.

Wolff, et al., Direct Gene Transfer Into Mouse Muscle in Vivo, Science, 1990, 247:1465-1468.

Wolff, et al., Conditions Affecting Direct Gene Transfer Into Rodent Muscle In Vivo, Biotechniques, 1991, 11 (4):474-485.

Zhang, et al., Efficient Expression of Naked DNA Delivered Intraarterially to Limb Muscles of Nonhuman Primates, Human Gene Therapy, 2001, 12:427-438.

Zhu, et al., Mass Spectrometric Characterization of the Human Androgen Receptor Ligand-Binding Domain Expressed in *Escherichia coli*, Biochemistry, 2001, 40:10756-10763.

PROSTATE CANCER VACCINE

CROSS-REFERENCE TO RELATED APPLICATIONS

This application is a continuation of U.S. patent application Ser. No. 14/614,137, filed on Feb. 4, 2015, which is a continuation of U.S. patent application Ser. No. 13/968,854, filed on Aug. 16, 2013, now U.S. Pat. No. 8,962,590, which is a continuation of U.S. patent application Ser. No. 13/031,396 filed on Feb. 21, 2011, now U.S. Pat. No. 8,513,210, which is a divisional of U.S. patent application Ser. No. 11/848,607 filed on Aug. 31, 2007, now U.S. Pat. No. 7,910,565 and claims the benefit of U.S. provisional application Ser. No. 60/841,769, filed on Sep. 1, 2006, all of which are herein incorporated by reference in their entirety.

STATEMENT REGARDING FEDERALLY SPONSORED RESEARCH OR DEVELOPMENT

This invention was made with government support under RR016489 awarded by the National Institutes of Health. The government has certain rights in the invention.

BACKGROUND OF THE INVENTION

Prostate cancer is a significant health risk for men over the age of 50, with about 200,000 newly diagnosed cases each year in the United States (Jemal A. et al., Cancer Statistics, 2005 (2005) CA Cancer J Clin, 55:10-30). It is the most common tumor diagnosed among men and the second leading cause of male cancer-related death in the United States (Jemal et al., Cancer Statistics, 2003 (2003) CA Cancer J Clin, 53:5-26). Despite advances in screening and early detection, approximately 30% of patients undergoing definitive prostatectomy or ablative radiation therapy will have recurrent disease at 10 years (Oefelein et al., 1997, J Urol, 158:1460-1465). At present, there is no accepted adjuvant treatment for patients undergoing radical prostatectomy or ablative radiation therapy that has been shown to prevent the progression to metastatic disease. In addition to new treatments for metastatic disease, new strategies are needed to eradicate microscopic disease to prevent the progression to clinically apparent metastasis.

In patients who have undergone definitive ablative therapy for prostate cancer, the presence of detectable serum levels of prostate-specific antigen (PSA) has provided a valuable indicator of microscopic metastatic disease. In a retrospective review of 1,997 men treated with radical prostatectomy, 15% were found to have evidence of a PSA-only recurrence over a median 5-year follow up, so-called stage D0 disease (Pound et al., 1999, JAMA 281:1591-7). Of these, 34% developed radiographically apparent metastatic disease, with a median time to development of metastatic disease of 8 years. In all patients with metastatic disease, the median time to death was 5 years (Pound et al., 1999, JAMA 281:1591-7). These findings suggest that patients with stage D0 disease are at high risk for progressive disease, however with a long window of time to test adjuvant therapies. Similarly, many patients are found to have microscopic pelvic lymph node metastases at the time of radical prostatectomy, so-called stage D1 disease. At present, the best treatment for these patients is controversial, with most treated with androgen deprivation, and others are expectantly observed without specific treatment. In retrospective studies, 10-year disease-specific recurrence and mortality is on the order of 50 to 66% for patients with stage D1 disease (Sgrignoli et al., 1994, J Urol, 152:1077-81; and Cadeddu et al., 1997, Urology, 50:251-5). This high-risk stage of minimal residual disease also provides an opportunity to test novel adjuvant therapies.

Immunological therapies, and vaccines in particular, are appealing as possible treatment options for prostate cancer for several reasons. Such therapies may be relatively safe and inexpensive treatments compared with chemotherapies for a disease for which no standard adjuvant treatments exist (Kent et al., Immunity of prostate specific antigens in the clinical expression of prostatic carcinoma (1976) In: Crispen R G, ed. Neoplasm immunity: mechanisms. Chicago, ITR, pp. 85-95; Guinan et al., 1984, Prostate, 5:221-230; and McNeel et al., 2000, Arch. Immunol. Ther. Exp., 48:85-93). Moreover, prostate cancer is a slow-growing disease, with typically over five years from the time of diagnosis of organ-confined disease to the development of clinically apparent metastatic disease. Such a slow-growing disease might be more amenable to vaccine-based treatments than a rapidly growing tumor, assuming that microscopic amounts of disease would be easier to treat than bulky or rapidly growing disease by vaccines. In fact, vaccines have already entered clinical trials for prostate cancer targeting a variety of prostate-specific proteins, with at least two dendritic cell-based vaccines suggesting clinical benefit in patients with low-volume metastatic disease (Murphy et al., 1999, Prostate, 39:54-59; and Small et al., 2000, J. Clin. Oncol. 18:3894-3903).

The use of plasmid DNA alone as a means of in vivo gene delivery by direct injection into muscle tissue was first described by Wolff et al. (Wolff et al., 1990, Science, 247:1465-1468). It was subsequently found that intramuscular or intradermal administration of plasmids expressing foreign genes elicited immune responses (Tang, et al., 1992, Nature, 356:152-154; Wang et al., 1993, Proc Natl. Acad. Sci. USA, 90:4156-4160; and Raz et al., 1994, Proc Natl. Acad. Sci. USA, 91:9519-9523). This has quickly led to numerous investigations into the use of plasmid DNA as a means of vaccine antigen delivery, both in animal and human models. DNA vaccines, like peptide-based vaccines, are relatively easy and inexpensive to manufacture, and are not individualized for patients as are dendritic cell-based vaccines. With recombinant protein vaccines, the antigen is taken up by antigen presenting cells and expressed predominantly in the context of MHC class II. DNA in nucleic acid vaccines is taken up and expressed by antigen-presenting cells directly, leading to antigen presentation through naturally processed MHC class I and II epitopes (Iwasaki, et al. 1997, J Immunol, 159:11-14). This direct expression by host cells, including MHC class I expressing bystander cells, has been demonstrated to lead to vigorous CD8+CTL responses specific for the targeted antigen (Iwasaki et al., 1997, J. Immunol. 159:11-14; Chen et al., 1998, J. Immunol., 160:2425-2432; Thomson et al., 1998, J. Immunol., 160:1717-1723; and Cho et al., 2000, Nat. Biotechnol. 18:509-514).

Clinical trials have suggested that plasmid DNA vaccines are safe and immunologically effective in humans. Boyer and colleagues reported that doses of 300 µg of plasmid DNA encoding HIV rev and env proteins administered intramuscularly were capable of eliciting antigen-specific, IFNγ-secreting T cell responses in HIV-seronegative patients (Boyer et al., 2000, J. Infect. Dis. 181:476-83). In addition, results of a clinical trial targeting prostate-specific membrane antigen (PSMA) in patients with prostate cancer by means of plasmid DNA and adenovirus have been reported (Mincheff et al., 2000, Eur. Urol., 38:208-217). In this study, 26 patients were immunized either in a prime/ boost strategy with an adenoviral vector expressing PSMA followed by immunization with plasmid DNA expressing PSMA, or with plasmid DNA alone. The authors report no significant toxicity with doses of 100-800 µg of plasmid DNA administered intradermally, and suggest that patients receiving plasmid DNA expressing PSMA and CD86 with soluble GM-CSF as an adjuvant were all successfully immunized.

A DNA vaccine for the treatment of prostate cancer based on prostatic acid phosphatase (PAP) has also been described (US 2004/0142890).

BRIEF SUMMARY OF THE INVENTION

The present invention is based, in part, on the inventors' discovery that patients with prostate cancer have antibodies specific for the androgen receptor, that androgen receptor ligand-binding domain as well as four fragments thereof (SEQ ID NO:9-12) can elicit immune responses in vivo, and that animals vaccinated with a DNA vaccine encoding the androgen receptor (AR) ligand-binding domain (LBD) inhibited prostate tumor growth in vivo.

In one aspect, the invention relates a method for inducing an immune reaction to androgen receptor in a mammal in need thereof, the method comprising administering to the mammal an effective amount of a recombinant DNA construct comprising a polynucleotide operatively linked to a transcriptional regulatory element (e.g., a promoter such as a heterologous promoter) wherein the polynucleotide encodes a member selected from (i) a mammalian androgen receptor (e.g., a human androgen receptor), (ii) a fragment of the androgen receptor that comprises the ligand-binding domain, (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12, whereby the mammal develops immune reaction against the androgen receptor. In one form, the polynucleotide employed in the method encodes the ligand-binding domain of a mammalian androgen receptor. In another form, multiple DNA constructs with each comprising a polynucleotide that encodes a different fragment selected from (iii)-(vi) are administered. For example, two DNA constructs covering fragments (iii) and (iv) can be administered together. As another example, four DNA constructs covering all four fragments (iii)-(vi) can be administered together. The method disclosed can be practiced with a mammal, preferably a human, who either currently has or previously had prostate cancer.

In one embodiment, the polynucleotide encodes a human androgen receptor or a fragment of the human androgen receptor that comprises the ligand-binding domain. The polynucleotide is preferably a nucleotide sequence of the human androgen receptor gene. In one form of this embodiment, the polynucleotide encodes the ligand-binding domain of a human androgen receptor.

The above method employing the DNA construct induces cytotoxic immune reaction against cells expressing androgen receptor. Preferably, both humoral and cellular immune reactions against androgen receptor are induced.

In another aspect, the present invention relates to a method for inducing an immune reaction to androgen receptor in a mammal in need thereof, the method comprising administering to the mammal an effective amount of a polypeptide selected from (i) a mammalian androgen receptor (e.g., a human androgen receptor), (ii) a fragment of the androgen receptor that comprises the ligand-binding domain, (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12, whereby the mammal develops immune reaction against the androgen receptor. In one form, the polypeptide employed is the ligand-binding domain of a mammalian androgen receptor. In another form, multiple fragments of the ligand-binding domain (e.g. SEQ ID NO:9 and SEQ ID NO:10, and optionally SEQ ID NO:11 and SEQ ID NO:12) are administered. The method disclosed can be practiced with a mammal, preferably a human, who either currently has or previously had prostate cancer.

In one embodiment, the human androgen receptor or a fragment of the human androgen receptor that comprises the ligand-binding domain is administered. In one form of this embodiment, the ligand-binding domain of the human androgen receptor is administered.

The above method employing the polypeptide induces cellular or humoral immune reaction against cells expressing androgen receptor. Preferably, both humoral and cellular immune reactions against androgen receptor are induced.

According to one embodiment of the invention, the recombinant DNA construct or the polypeptide is administered to the mammal intradermally, intramuscularly, subcutaneously, or intravascularly, including intravenously and intraarterially. Preferably, the recombinant DNA construct is administered intradermally, intramuscularly, or intravascularly and the polypeptide is administered subcutaneously.

In another aspect, the present invention relates to an isolated polypeptide selected from SEQ ID NO:9, SEQ ID NO:10, SEQ ID NO:11, and SEQ ID NO:12. In another aspect, the present invention relates to a composition that comprises one or more of the above polypeptides and a pharmaceutically acceptable carrier.

According to another aspect of the present invention, a DNA vaccine is contemplated which comprises a plasmid vector comprising a polynucleotide operatively linked to a transcriptional regulatory element (e.g., a promoter such as a heterologous promoter) wherein the polynucleotide encodes a member selected from (i) a mammalian androgen receptor (e.g., a human androgen receptor), (ii) a fragment of the androgen receptor that comprises the ligand-binding domain, (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12, wherein upon administration of said vaccine to a mammal a cytotoxic immune reaction against cells expressing androgen receptor is induced. The vaccine of the present invention preferably is suitable for intradermal, intramuscular, subcutaneous, or intravascular (including intravenous and intraarterial) administration to a mammal such as a human. According to a preferred embodiment, the plasmid vector comprises (a) a backbone of pNGVL3, (b) a polynucleotide operably inserted therein wherein the polynucleotide encodes a member selected from (i) a mammalian androgen receptor (e.g., a human androgen receptor), (ii) a fragment of the androgen receptor that comprises the ligand-binding domain, (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12, and, optionally, (c) one or a plurality of an immunostimulatory sequence (ISS) motif.

Preferably, the DNA vaccine according to the invention comprises a plasmid vector that comprises (a) a polynucleotide operatively linked to a CMV promoter wherein the polynucleotide encodes a member selected from (i) a mammalian androgen receptor (e.g., a human androgen receptor), (ii) a fragment of the androgen receptor that comprises the ligand-binding domain, (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12, (b) a CMV intron A operatively linked to the polynucleotide for enhancing expression of the polynucleotide, and, optionally, (c) at least one copy of an immunostimulatory fragment comprising 5'-GTCGTT-3'. In one embodiment, the plasmid construct does not express in eukaryotic cells any gene other than a member selected from (i) a mammalian androgen receptor, (ii) a fragment of the androgen receptor that comprises the ligand-binding domain, (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12. The plasmid vector pTVG4 is particularly preferred.

According to another aspect of the present invention, a peptide vaccine is contemplated which comprises a member selected from (i) a mammalian androgen receptor (e.g., a human androgen receptor), (ii) a fragment of the androgen receptor that comprises the ligand-binding domain, (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12. The peptide vaccine also comprises a pharmaceutically acceptable carrier. The peptide vaccine preferably is suitable for intradermal, intramuscular, subcutaneous, or intravascular (including intravenous and intraarterial) administration to a mammal such as a human.

Also disclosed are pharmaceutical compositions comprising a DNA or peptide vaccine of the invention (the polypeptides or recombinant plasmid vectors described above), and a pharmaceutically acceptable carrier. Preferably, the pharmaceutical composition further comprises a suitable amount of immuno-stimulant such as GM-CSF.

A kit containing the DNA or peptide vaccine of the invention and an instruction manual directing administering the vaccine to a mammal that has or previously had prostate cancer (e.g., a human prostate cancer patient) is also within the scope of the invention.

In another aspect, the present invention relates to a method for determining the effectiveness of a treatment for prostate cancer. The method includes the steps of (a) measuring the frequency or amount of cytotoxic T lymphocytes (CTLs) specific for a peptide selected from SEQ ID NO:9, SEQ ID NO:10, SEQ ID NO:11, and SEQ ID NO:12 prior to providing at least a portion of the treatment to a mammal (e.g., a human) having prostate cancer, (b) measuring the frequency or amount of CTLs specific for the peptide after said portion of the treatment is provided to the mammal, and (c) comparing the frequency or amount of CTLs of (a) and that of (b) wherein the frequency or amount of CTLs of (b) being higher than that of (a) indicates that the treatment is effective.

DETAILED DESCRIPTION OF THE INVENTION

Figure 1:
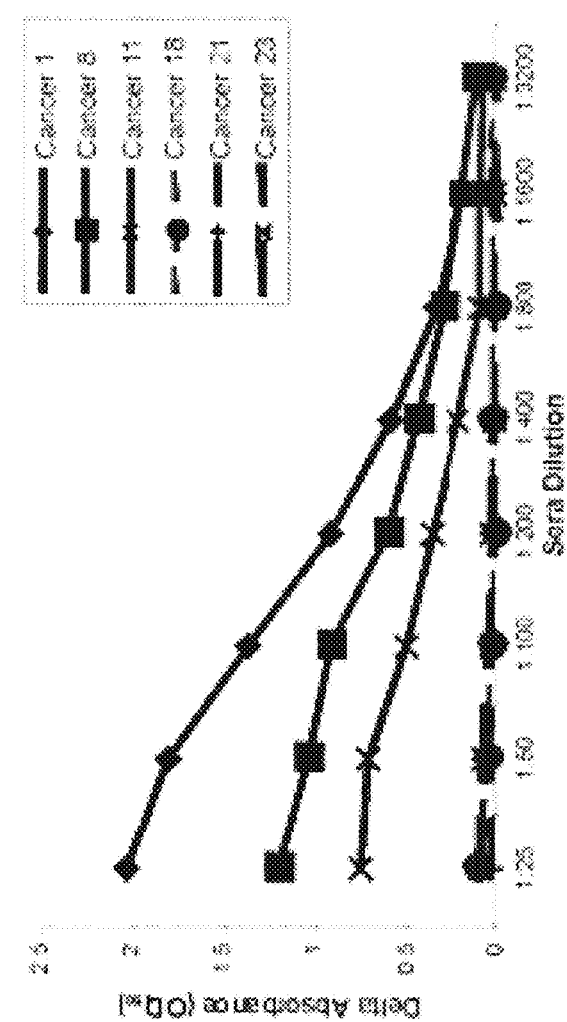
FIG. 1 shows that patients with prostate cancer have antibodies specific for the androgen receptor. Panel A: Sera from patients with various stages of prostate cancer were analyzed for the presence of AR-specific antibodies by screening titrated sera samples using ELISA. Panel B: The presence or absence of AR-specific antibodies was confirmed using Western blotting against thioredoxin-tagged AR LBD or thioredoxin (trx) alone, followed by incubation with patient's sera. Panel C: ELISA was used to evaluate sera samples for the presence of AR-specific antibodies. Samples were analyzed from healthy male blood donors (n=41), patients with prostatitis (n=38), or patients with prostate cancer (n=105), and relative antibody concentrations were calculated by referencing delta absorbance values to titrated Ig protein standards. Positive antibody responses were defined by values higher than three standard deviations above the mean of the healthy donor group (greater than 0.22 µg/mL, indicated by the line). Statistically significant differences were calculated using the Chi square test.
Figure 1:
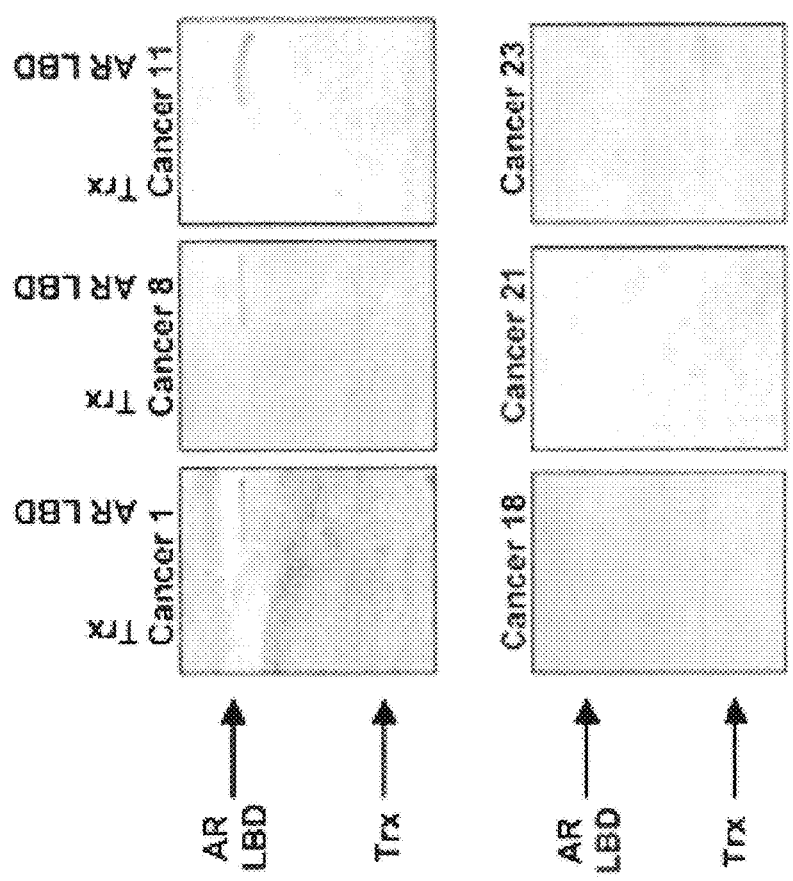
Figure 1:
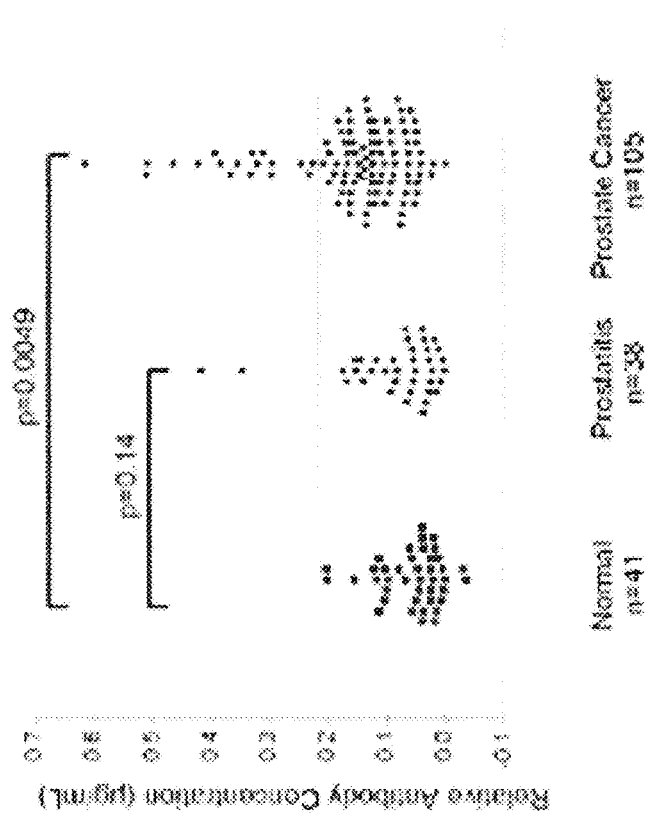

This invention provides pharmaceutical compositions and methods that relate to the use of plasmid DNA and peptide vaccines for the treatment of prostate cancer. Specifically, this invention provides polypeptides such as the ligand-binding domain of an androgen receptor or certain fragments thereof and recombinant plasmid vectors comprising genes or polynucleotide molecules encoding the polypeptides for preventing or treating prostate cancer, including metastatic tumors thereof. In a preferred embodiment, the polypeptides or recombinant plasmid vectors are administered to prostate cancer patients to treat prostate cancer. In another preferred embodiment, the polypeptides or recombinant plasmid vectors are administered to stage D0 or D1 prostate cancer patients to prevent recurrence or metastasis of prostate cancer.

A polypeptide vaccine of the present invention, which comprises a pharmaceutically acceptable carrier and an effective amount of a mammalian androgen receptor, a fragment of the mammalian androgen receptor that comprises the ligand-binding domain, or certain fragments of the ligand-binding domain, can be administered into a mammal such as a human being to elicit an immune response against androgen receptor in the mammal. An "effective amount" or an "immunologically effective amount" means that the administration of that amount to a subject, either in a single dose or as part of a series, is effective for inducing an immune reaction and preferably for treating or preventing prostate cancer. Pharmaceutically acceptable carriers are well known to those of ordinary skill in the art (Arnon, R. (Ed.) Synthetic Vaccines 1:83-92, CRC Press, Inc., Boca Raton, Fla., 1987). They include liquid media suitable for use as vehicles to introduce the peptide into a patient but should not in themselves induce the production of antibodies harmful to the individual receiving the composition. An example of such liquid media is saline solution. Moreover, the vaccine formulation may also contain an adjuvant for stimulating the immune response and thereby enhancing the effect of the vaccine.

The plasmid DNA vaccines of the present invention, when directly introduced into mammals such as humans in vivo, induce the expression of encoded polypeptides within the mammals, and cause the mammals' immune system to become reactive against the polypeptides. The vaccines may be any polynucleotides that are capable of eliciting immune responses to an encoded polypeptide.

The instant invention also provides a method of using a polynucleotide which, upon introduction into a mammal, induces the expression, in vivo, of the polynucleotide thereby producing the encoded polypeptide, and causes the mammal to become immune reactive against the polypeptide so produced.

DNA vaccines, like peptide-based vaccines, are relatively easy and inexpensive to manufacture, and are not individualized for patients, as are dendritic cell-based vaccines. With recombinant protein vaccines, the antigen is taken up by antigen presenting cells and expressed predominantly in the context of MHC class II. DNA in nucleic acid vaccines is taken up and expressed by antigen-presenting cells directly, leading to antigen presentation through naturally processed MHC class I and II epitopes (Iwasaki, et al. 1997, J Immunol, 159:11-14).

Given their potential ability to elicit antigen-specific cytotoxic T lymphocytes (CTL) immunity in an MHC class I diverse population, DNA-based vaccines for various diseases have recently entered human clinical trials (Mincheff et al., 2000, Eur. Urol., 38:208-217). This method of immunization is similar to the use of viral immunization vectors, but without the additional foreign antigens introduced with a viral vector and therefore with less risk of an overwhelming immune response to the vector itself (Irvine and Restifo, 1995, Seminars in Canc. Biol. 6:337-347). Direct expression by host cells, including MHC class I-expressing bystander cells, has been demonstrated to lead to vigorous CD8+CTL responses specific for the targeted antigen (Iwasak et al., 1997, J. Immunol. 159:11-4; Chen et al., 1998, J. Immunol. 160:2425-2432; Thomson et al., 1998, J. Immunol. 160: 1717-1723; and Cho et al., 2000, Nat. Biotechnol, 18:509-14). In addition, plasmid DNA used for immunization may remain within cells at the site of immunization, providing a constant source of antigenic stimulation. Persistent antigen expression may lead to long-lived immunity (Raz et al., 1994, Proc. Natl. Acad. Sci. USA 91:9519-23).

The present invention provides DNA-based vaccines that express a polypeptide antigen, the ligand-binding domain of a mammalian androgen receptor or certain fragments thereof, and methods for treating prostate cancers in a human or non-human animal using the vaccines. In addition to the reasons explained above, plasmid vaccines are advantageous over viral vaccines. For example, viral vaccines are not amenable to repeated immunizations. With viral vectors, one is trying to elicit an immune response against a "self" protein encoded by a foreign virus. The immune system preferentially recognizes the foreign proteins, sometimes hundreds of proteins, encoded by the virus. For example, the inventors have found in rats that repeated immunizations with a vaccinia virus encoding human prostatic acid phosphatase (hPAP) elicits a strong vaccinia response but no hPAP-specific response (Johnson et al., 2007, Canc. Immunol. Immunoth. 56:885). That same finding was also shown in humans, in a trial in which repeated immunization with the vaccinia virus encoding human prostate-specific antigen (PSA) elicited weak PSA-specific immunity, but potent vaccinia immunity (Sanda et al., 1999, Urology 53:260). The direction in the field of viral-based vaccines is to "prime" with a virus encoding the antigen, and then "boost" with a different virus (like adenovirus or fowl pox) encoding the same antigen. The advantage of plasmid DNA vaccines is that they encode a defined, often small, number of proteins. Therefore, one can repetitively immunize the animal or patient. Furthermore, a virus may kill cells, incorporate into the genome, or potentially induce other unwanted immune responses. All these are disadvantages that are likely avoided by DNA plasmid vaccines.

It is readily recognizable that the ligand-binding domain of an androgen receptor of any origin, or any of the ligand-binding domain's derivatives, equivalents, variants, mutants etc., is suitable for the instant invention, as long as the ligand-binding domain or derivatives, equivalents, variants, or mutants thereof is able to induce an immune reaction in the host human or non-human animal substantially similar to that induced by an autoantigenic or xenoantigenic ligand-binding domain of the androgen receptor in the animal. Similarly, a polynucleotide sequence of an androgen receptor gene of any origin that encodes the ligand-binding domain of the receptor, or any of the polynucleotide's derivatives, equivalents, variants, mutants etc., is suitable for the instant invention, as long as the polynucleotide sequence and the polypeptide or protein encoded by the polynucleotide sequence, or derivatives, equivalents, variants, or mutants thereof is able to induce an immune reaction in the host human or non-human animal substantially similar to that induced by an autoantigenic or xenoantigenic ligand-binding domain of the androgen receptor in the animal.

Androgen receptor genes are known and have been cloned from many species. For example, the human, mouse, rat, dog, chimpanzee, macaque, and lemur androgen receptor cDNA along with amino acid sequences can be found at GenBank Accession Nos. NM_000044 (cDNA-SEQ ID NO:1 and amino acid sequence-SEQ ID NO:2), NM_013476 (cDNA-SEQ ID NO:3 and amino acid sequence-SEQ ID NO:4), NM_012502 (cDNA-SEQ ID NO:5 and amino acid sequence-SEQ ID NO:6), NM_001003053, NM_001009012, U94179, and U94178, respectively. Androgen receptor genes from other species are also known. These species include but are not limited to *Sus scrofa, Astatotilapia burtoni, Gallus gallus, Kryptolebias marmoratus, Alligator mississippiensis, Leucoraja erinacea, Haplochromis burtoni, Pimephales promelas, Dicentrarchus labrax, Gambusia affinis, Micropogonias undulates, Oryzias latipes, Acanthopagrus schlegelii, Rana catesbeiana, Crocuta crocuta, Eulemur fulvus collaris,* and *Anguilla japonica* (see GenBank Accession Nos. NM_214314 (or AF161717), AY082342, NM_001040090, DQ339105, AB186356, DQ382340, AF121257, AY727529, AY647256, AB099303, AY701761, AB076399, AY219702, AY324231, AY128705, U94178, and AB023960, respectively). The ligand-binding domains of androgen receptors are well known in the art. For the purpose of the present invention, the ligand-binding domain of the human androgen receptor refers to a polypeptide that starts at any amino acid from amino acid positions 651 to 681 and ends at any amino acid from amino acid positions 900 to 920. For example, human androgen receptor or a fragment of the human androgen receptor that comprises amino acids 681-900 as well as DNA vaccines containing a polynucleotide encoding the above are suitable vaccines. The corresponding ligand-binding domains of androgen receptors from other species can be readily determined by sequence alignment (to the human sequence) (e.g., by the methods described below in connection with sequence identity or homology). In a preferred embodiment, a polypeptide from the human androgen receptor that starts at any amino acid from amino acid positions 661 to 671 and ends at any amino acid from amino acid positions 910 to 920 is used in the present invention. In a more preferred embodiment, a polypeptide containing amino acids 661 to 920 or 664 to 920 of the human androgen receptor is used in the present invention. To help determine the corresponding fragments of the androgen receptors from other species, it is noted here that the amino acid positions on rat, dog, chimpanzee, macaque, and lemur androgen receptors that correspond to amino acid positions 661 to 920 of the human androgen receptor are 640 to 899, 643 to 902, 648 to 907, 652 to 910, 636 to 895, and 625 to 884, respectively. It is noted that the above fragments of the human, mouse, rat, dog, chimpanzee, macaque, and lemur androgen receptors have the same amino acid sequence. The ligand-binding domains of the androgen receptors of other species are also known or can be readily identified through sequence alignment. As will be readily recognized by one of ordinary skill in the art, any DNA sequence that encodes a ligand-binding domain or a larger fragment of an androgen receptor including the full-length receptor from one of the above species as well as other animals is suitable for the present invention.

As is well-known to those skilled in the art, polypeptides having substantial sequence similarities cause identical or very similar immune reaction in a host animal. As discussed below, this phenomenon is the basis for using a xenoantigen for inducing autoreactive reaction to an otherwise tolerated autoantigen. Accordingly, a derivative, equivalent, variant, fragment, or mutant of the ligand-binding domain of any of the known or to-be-identified androgen receptors or any DNA sequence encoding the above is also suitable for the present invention. The polypeptides encoded by these DNA sequences are useful as long as the polypeptides encoded by the DNA sequences are structurally similar to the ligand-binding domain of the autologous androgen receptor, and are sufficiently immunogenic.

It is readily apparent to those ordinarily skilled in the art that variations or derivatives of the nucleotide sequence encoding the polypeptide or protein antigen can be produced which alter the amino acid sequence of the encoded polypeptide or protein. The altered polypeptide or protein may have an altered amino acid sequence, for example by conservative substitution, yet still elicits immune responses which react with the unaltered protein antigen, and are considered functional equivalents. According to a preferred embodiment, the derivative, equivalents, variants, or mutants of the ligand-binding domain of an androgen receptor are polypeptides that are at least 85% homologous to the ligand-binding domain of a human androgen receptor. More preferably, the homology is at least 88%, at least 90%, at least 95%, or at least 98%.

As used in this application, "percent identity" between amino acid or nucleotide sequences is synonymous with "percent homology," which can be determined using the algorithm of Karlin and Altschul (Proc. Natl. Acad. Sci. USA 87, 2264-2268, 1990), modified by Karlin and Altschul (Proc. Natl. Acad. Sci. USA 90, 5873-5877, 1993). The noted algorithm is incorporated into the NBLAST and XBLAST programs of Altschul et al. (J. Mol. Biol. 215, 403-410, 1990). BLAST nucleotide searches are performed with the NBLAST program, score=100, wordlength=12, to obtain nucleotide sequences homologous to a polynucleotide of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (Nucleic Acids Res. 25, 3389-3402, 1997). When utilizing BLAST and Gapped BLAST programs, the default parameters of the respective programs (e.g., XBLAST and NBLAST) are used.

As used herein, the term "conservative substitution" denotes the replacement of an amino acid residue by another, biologically similar residue. It is well known in the art that the amino acids within the same conservative group can typically substitute for one another without substantially affecting the function of a protein. For the purpose of the present invention, such conservative groups are set forth in Table 1 based on shared properties.

TABLE 1

| Conservative substitution. | |
|---|---|
| Original Residue | Conservative Substitution |
| Ala (A) | Val, Leu, Ile |
| Arg (R) | Lys, Gln, Asn |
| Asn (N) | Gln, His, Lys, Arg |

TABLE 1-continued

| Conservative substitution. | |
|---|---|
| Original Residue | Conservative Substitution |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

In addition, fragments of a ligand binding domain of an androgen receptor such as those that can bind to HLA-A2 are also useful antigens which elicit cytotoxic responses against cells expressing the androgen receptor or its ligand binding domain. Polynucleotides that encode these fragments are considered functional equivalents. Examples of these fragments are provided in the examples below. In particular, the use of the following four fragments are contemplated: SEQ ID NO:9 (amino acids 811-819 of SEQ ID NO:2), SEQ ID NO:10 (amino acids 761-770 of SEQ ID NO:2), SEQ ID NO:11 (amino acids 805-813 of SEQ ID NO:2), and SEQ ID NO:12 (amino acids 859-867 of SEQ ID NO:2).

A polynucleotide useful in the present invention is preferably ligated into an expression vector which has been specifically optimized for polynucleotide vaccinations. Elements include a transcriptional promoter, immunogenic epitopes, and additional cistrons encoding immunoenhancing or immunomodulatory genes, with their own promoters, transcriptional terminator, bacterial origin of replication and antibiotic resistance gene, as well known to those skilled in the art. Optionally, the vector may contain internal ribosome entry sites (IRES) for the expression of polycistronic mRNA.

In one embodiment of this invention, a polynucleotide useful in the present invention is directly linked to a transcriptional promoter. The use of tissue-specific promoters or enhancers, for example the muscle creatine kinase (MCK) enhancer element, may be desirable to limit expression of the polynucleotide to a particular tissue type. For example, myocytes are terminally differentiated cells which do not divide. Integration of foreign DNA into chromosomes appears to require both cell division and protein synthesis. Thus, limiting protein expression to non-dividing cells such as myocytes may be preferable. In addition, a PSA promoter may be used to limit expression of the protein to prostate tissue. In one embodiment, tissue- or cell-specific promoters may be used to target the expression of the protein to antigen-presenting cells. For example, an α-fetoprotein (AFP) promoter (see e.g., Peyton et al. 2000, Proc. Natl. Acad. Sci., USA. 97:10890-10894) may be used to limit expression to liver tissues. However, use of the CMV promoter is adequate for achieving expression in many tissues into which the plasmid DNA vaccine is introduced.

Suitable vectors include any plasmid DNA construct encoding an androgen receptor, a fragment of the androgen receptor that comprises the ligand-binding domain, a suitable fragment of the ligand-binding domain, or a functional equivalent or derivative thereof, operatively linked to a suitable promoter. Examples of such vectors include the pCMV series of expression vectors, commercially available from Stratagene (La Jolla, Calif.); or the pCDNA or pREP series of expression vectors by Invitrogen Corporation (Carlsbad, Calif.).

A preferred vector is pNGVL3 available from the National Gene Vector Laboratory at the University of Michigan. This vector, similar to the pCDNA3.1 eukaryotic expression vector of Invitrogen Corp. (Carlsbad, Calif.), drives transcription from the CMV promoter, but also includes the CMV intron A sequence to enhance protein expression (Lee et al., 1997, Mol. Cells 7:495-501). The vector also contains a multi-cloning site, and does not express a eukaryotic antibiotic resistance gene, such that the only protein expression expected in a eukaryotic system is the one driven from the CMV promoter, unlike the pCDNA vector. Another preferred vector is the pTVG4 vector described in US 2004/0142890, which is herein incorporated by reference in its entirety. The pTVG4 vector can be made by incorporating 2 copies of a 36-bp immunostimulatory (ISS) fragment containing the 5'-GTCGTT-3' motif previously identified (Hartmann et al., 2000, J. Immunol. 164: 1617-24) into pNGVL3.

There are many embodiments of the instant invention which those skilled in the art can appreciate from the specification. Thus, different transcriptional promoters, terminators, and other transcriptional regulatory elements may be used successfully. Examples of other eukaryotic transcription promoters include the Rous sarcoma virus (RSV) promoter, the simian virus 40 (SV40) promoter, the human elongation factor-1α (EF-1α) promoter, and the human ubiquitin C (UbC) promoter.

A Kozak sequence can be provided upstream of the polynucleotide useful in the present invention to enhance the translation of the corresponding mRNA from the polynucleotide. For vertebrates, the Kozak sequence is (GCC)NCCATGG (SEQ ID NO:7) wherein N is A or G and GCC is less conserved. For example, ACCATGG can be used. See Kozak, M. Nucleic Acids Res. 1987, 15:8125-48.

The vectors of the present invention may be delivered intradermally, intramuscularly, subcutaneously, or intravascularly (including intravenously and intraarterially). In preferred embodiments, delivery may be a combination of two or more of the various delivery methods.

"Naked" plasmid DNA expressing a transgene could be directly injected intradermally or intramuscularly, taken up, and expressed (see e.g., Wolff et al., 1990, Science 247: 1465-8). The efficiency of this approach may be low, with only a small percentage of myocytes being directly transformed in vivo, and within only a limited area of muscle tissue targeted by this directed delivery. Various alternative approaches yielding a higher gene delivery efficiency are known (see e.g., Acsadi et al., 1991, New Biol. 3:71-81). Subsequent work on strategies that increase uptake of plasmid DNA by muscle tissue focused on various carrier solutions and molecules (Wolff et. al., 1991, Biotechniques 11:474-85; and Budker et. al., 1996, Nat. Biotechnol. 14:760-4), the use of myotoxic agents to enhance DNA uptake (Davis et al., 1993, Hum. Gene Ther. 4:151-9; and Danko et al., 1994, Gene Ther. 1:114-21), and the use of various transcriptional promoters and plasmid DNA backbones (Manthorpe et al., 1993, Hum. Gene Ther. 4:419-31).

In a preferred embodiment, plasmid vectors of the present invention may be delivered to the patient in need thereof intravascularly. Plasmid DNA delivered intravascularly resulted in 100-fold higher uptake in downstream tissues in rodent studies (Budker et al., 1996, Gene Ther. 3:593-8). Intravascular delivery may be intravenal, e.g. by direct injection of plasmid DNA into the portal vein of rodents with uptake and expression demonstrated in hepatocytes (Budker et al., 1996, Gene Ther. 3:593-8; and Zhang et al., 1997, Hum. Gene Ther. 8:1763-72). Intravascular delivery may also be performed more directly by intraarterial delivery. For example, initial studies in rodents demonstrated that high levels of gene expression in hind limb muscle could be obtained by rapid injection of plasmid DNA into the femoral artery (Budker et al., 1998, Gene Ther. 5:272-276). This approach is efficient and safe in non-human primates as well, with an average of 7% of downstream myofibers expressing a β-galactosidase reporter construct two weeks after intraarterial DNA administration (Zhang et al., 2001, Hum. Gene Ther. 12:427-438). Parallel studies in T cell immuno-suppressed rats showed that gene expression was stable for at least 10 weeks (Zhang et al., 2001, Hum. Gene Ther. 12:427-438).

Accordingly, delivery of plasmid DNA vaccines of the present invention can be done by direct intraarterial administration. This method provides more effective delivery to MHC class I expressing cells. Administrations of plasmid DNA vaccines intravascularly may result in increased antigen expression and subsequently lead to enhanced immune responses, and increased antigen expression in MHC class I expressing cells by means of intraarterial delivery of DNA plasmid may lead to a more robust immune response with androgen receptor-specific CTL. An intraarterial method of DNA delivery has been shown to be at least as effective as or more effective than traditional intradermal administration of DNA in eliciting prostatic acid phosphatase-specific immunity.

In another embodiment, intravenous delivery may also be used, employing methods well known to those skilled in the art (See e.g., Budker et al., 1998, Gene Ther. 5:272-276; and Budker et al., 1996, Gene Ther. 3:593-598). This delivery method may lead to a high level of antigen expression in hepatocytes. Expression of the antigen in liver, a tissue more rich with antigen-presenting cells, may lead to a more pronounced Th1/CTL response than expression in muscle tissue.

The DNA or peptide vaccines of the present invention can be used in a prime-boost strategy to induce robust and long-lasting immune response to androgen receptor. Priming and boosting vaccination protocols based on repeated injections of the same antigenic construct are well known and result in strong CTL responses. In general, the first dose may not produce protective immunity, but only "primes" the immune system. A protective immune response develops after the second or third dose.

In one embodiment, the DNA or peptide vaccines of the present invention may be used in a conventional prime-boost strategy, in which the same antigen is administered to the animal in multiple doses. In a preferred embodiment, the DNA or peptide vaccine is used in one or more inoculations. These boosts are performed according to conventional techniques, and can be further optimized empirically in terms of schedule of administration, route of administration, choice of adjuvant, dose, and potential sequence when administered with another vaccine, therapy or homologous vaccine.

The peptide or DNA vaccines of the present invention may be used in a prime-boost strategy using an alternative administration of xenoantigen and autoantigen or xenoantigen- and autoantigen-encoding vectors. Specifically, according to the present invention, the animal is first treated, or "primed," with a peptide antigen of foreign origin (a "xenoantigen") or DNA vaccine encoding the antigen of foreign origin. The animal is then treated with another peptide antigen which corresponds to the xenoantigen but is of self origin ("autoantigen") or another DNA vaccine encoding the autoantigen. This way, the immune reaction to the antigen is boosted. The boosting step may be repeated one or more times.

A xenoantigen, as compared to a self-antigen or an autoantigen, is an antigen originated in or derived from a species different from the species that generates an immune reaction against the antigen. Xenoantigens usually are highly homologous molecules to a corresponding autoantigen. Xenoantigens have been shown to be able to elicit auto-reactive immunity. For example, molecular mimicry by highly homologous viral antigens has been one theory to explain the occurrence of several autoimmune diseases (von Herrat and Oldstone, 1996, Curr. Opin. Immunol. 8:878-885; and Oldstone, 1998, Faseb J. 12:1255-1265). That is, the induction of immune responses following infection by viral antigens that closely resemble normal autologous proteins may then lead to an autoimmune reaction to the autologous protein.

The use of highly homologous foreign antigens or xenoantigens as vaccine antigens to elicit autoreactive immunity has been explored in animal models. For example, xenoantigens derived from zona pellucida of foreign species can elicit autoreactive T cell responses and disrupt ovarian function in a variety of animal species studied (Mahi-Brown et al., 1992, J. Reprod. Immunol. 21:29-46; and Mahi-Brown, 1996, J. Reprod. Fertil. Suppl. 50:165-74). While not wishing to be bound by any theory on mechanism, it is believed that because T cells involved in autoimmune processes recognize peptide epitopes presented in the context of MHC molecules, the uptake and MHC presentation of a homologous foreign antigen presumably exposes T cell epitopes with enhanced MHC binding or unmasks cryptic epitopes of the native antigen not normally recognized.

While the prime-boost strategy is known to work with antigens of different origins, it is readily apparent to those ordinarily skilled in the art that variants, derivatives or equivalents, as discussed above, of the nucleotide sequence encoding a self-antigen can also be used to achieve the same results as xenoantigens.

The peptide or DNA vaccines of the present invention may be used together with prostate cancer vaccines based on other antigens such as prostatic acid phosphatase-based antigens. The androgen receptor-based vaccines and vaccines based on other antigens can be used simultaneously or at different times. Each may be used in a prime-boost strategy.

The present invention also provides a method for determining the effectiveness of a treatment for prostate cancer. The method includes the steps of (a) measuring the frequency or amount of cytotoxic T lymphocytes (CTLs) specific for a peptide selected from SEQ ID NO:9, SEQ ID NO:10, SEQ ID NO:11, and SEQ ID NO:12 prior to providing at least a portion of the treatment to a mammal having prostate cancer, (b) measuring the frequency or amount of CTLs specific for the peptide after said portion of the treatment is provided to the mammal, and (c) comparing the frequency or amount of CTLs of (a) and that of (b) wherein the frequency or amount of CTLs of (b) being higher than that of (a) indicates that the treatment is effective. For example, a biological sample containing CTLs such as a blood sample or a sample of peripheral blood mononuclear cells (PBMC) can be taken from the mammal and the frequency or amount of CTLs in the blood sample can be measured. In one embodiment, the method is used to determine the effectiveness of a treatment provided to a human prostate cancer patient.

One of ordinary skill in the art is familiar with the techniques for functional and quantitative measurements of antigen-specific T cells. Examples include but are not limited to limited dilution assays (LDA), enzyme linked immunosorbent assay on a single cell level (ELISPOT), intracellular staining, and MHC/HLA multimer (e.g., dimer, tetramer, and pentamer) staining. Description on the MHC/HLA multimer staining technique can be found, for example, in Arnold H Bakker and Ton N M Schumacher (Current Opinion in Immunology, 2005, 17:428-433), Meidenbauer N et al. (Methods, 2003, 31:160-171), and U.S. patent application publication 20072036812.

In one embodiment, a biological sample (e.g., a blood sample or PBMC sample) containing CTLs from a patient is obtained and the sample is brought into contacted with an HLA multimer (e.g., an HLA tetramer). The frequency or amount of CTLs specific for a peptide antigen bound to the HLA tetramer can then be measured by known techniques such as flow cytometry.

The invention will be more fully understood upon consideration of the following non-limiting examples.

Example 1

Figure 2:
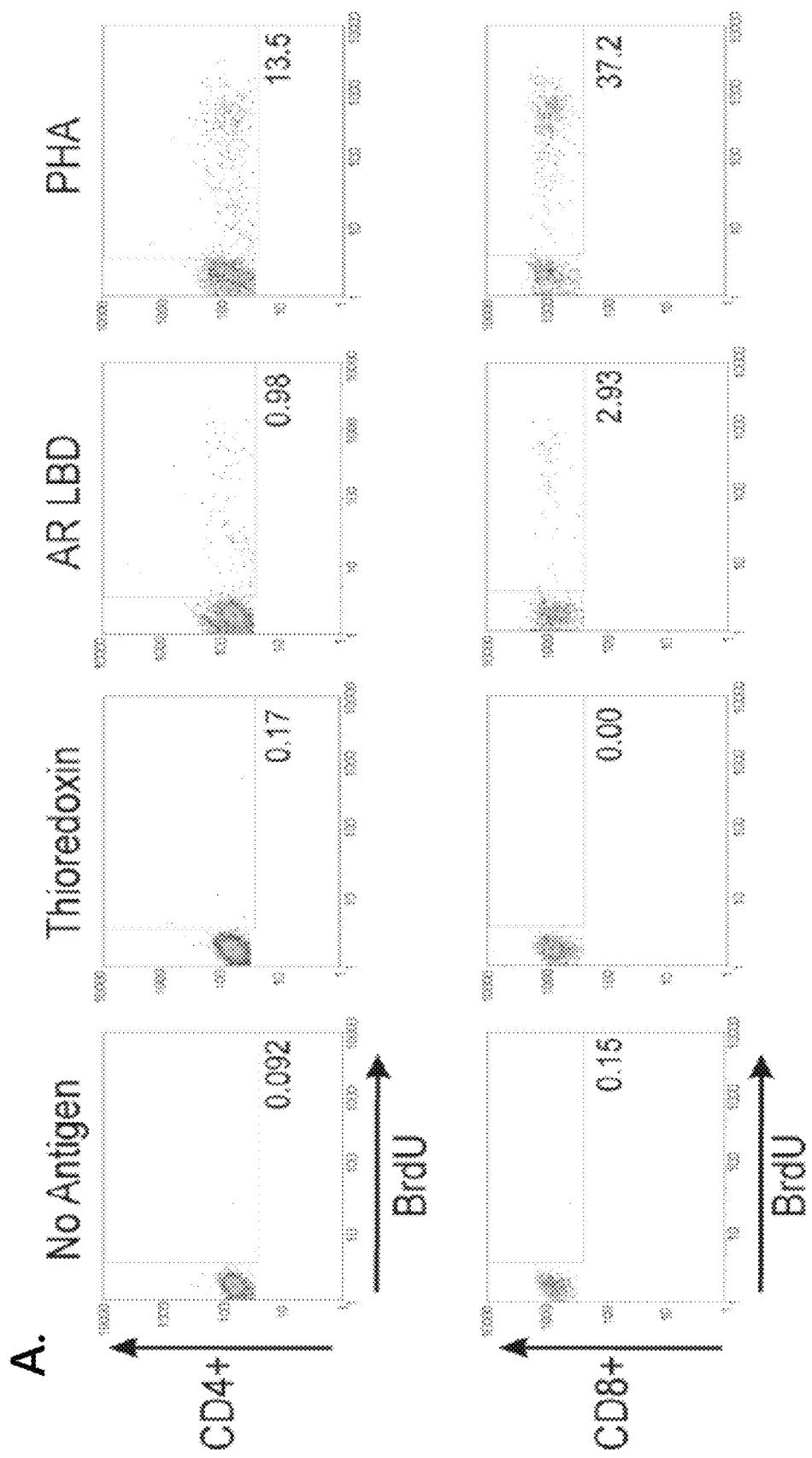
FIG. 2 shows that patients with AR LBD-specific IgG antibodies have concurrent AR-specific cellular immune responses. PBMC were analyzed for the presence of AR-specific T cells and IFNγ-secreting cells among patients with antibody responses specific for the AR (n=6) or patients with no detectable antibody responses (n=9). PBMC were stimulated with thioredoxin-tagged AR LBD, thioredoxin alone, media only, or PHA. After a 96-hour stimulation, these cells were analyzed for the presence of CD4+ and CD8+ T cell proliferation in response to antigen stimulation. Example data is shown in panel A from a subject with a strong $IgG_2$ response. The numbers in the upper-right corner of each panel indicate the percentage of CD4+ or CD8+ T cells that co-stained with BrdU. Proliferation indexes (PI) were calculated by normalizing experimental values to values obtained from PBMCs stimulated with media alone, and compiled PI values are shown for CD4+ (panel B, left) and CD8+ (panel B, right) T-cells. Supernatants from cultured PBMC were also analyzed for the presence of IFNγ secretion by capture ELISA (panel C). A comparison of results among different antigen-stimulation conditions was performed using the Student's T test.
Figure 2:
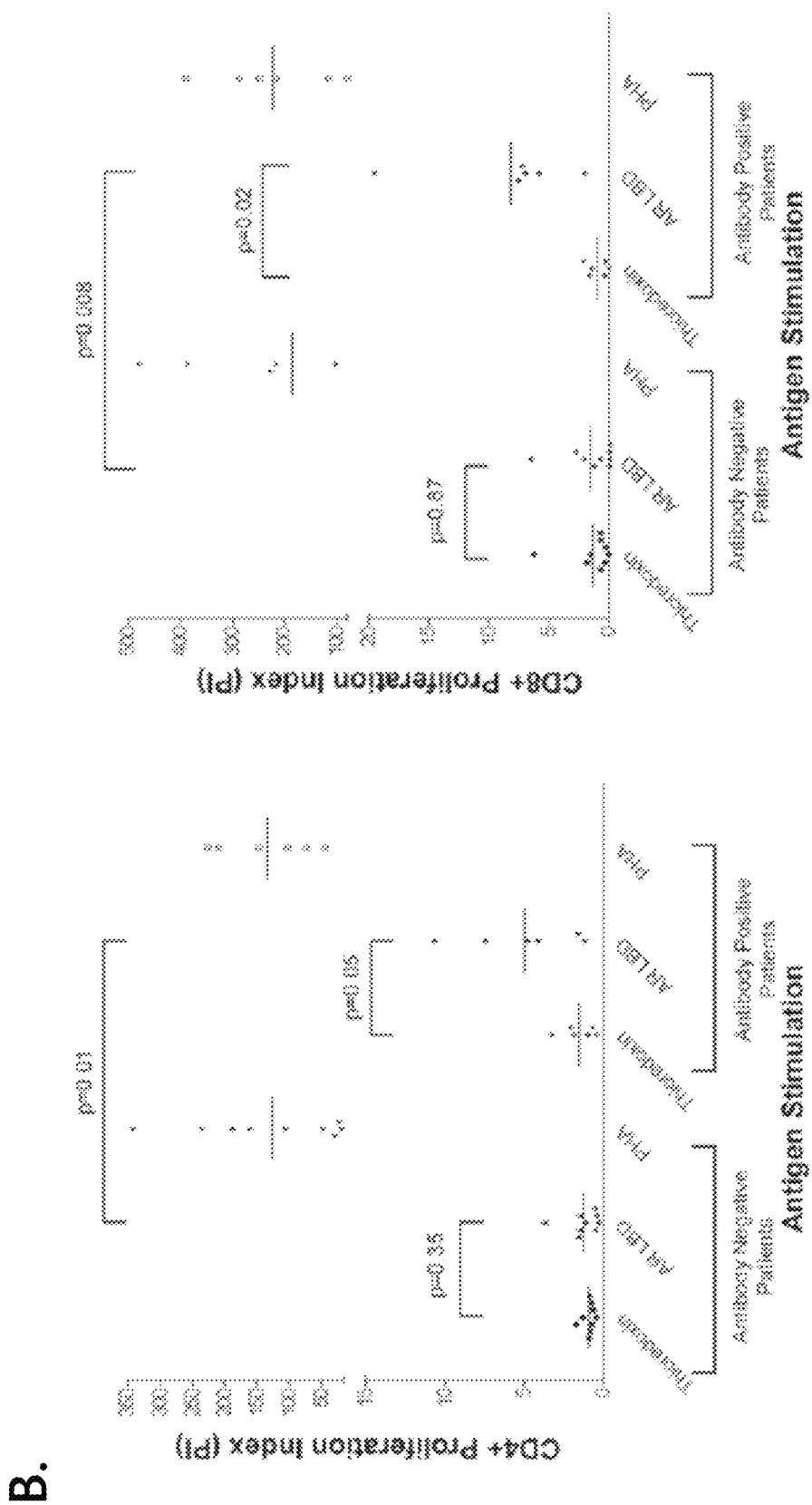
Figure 2:
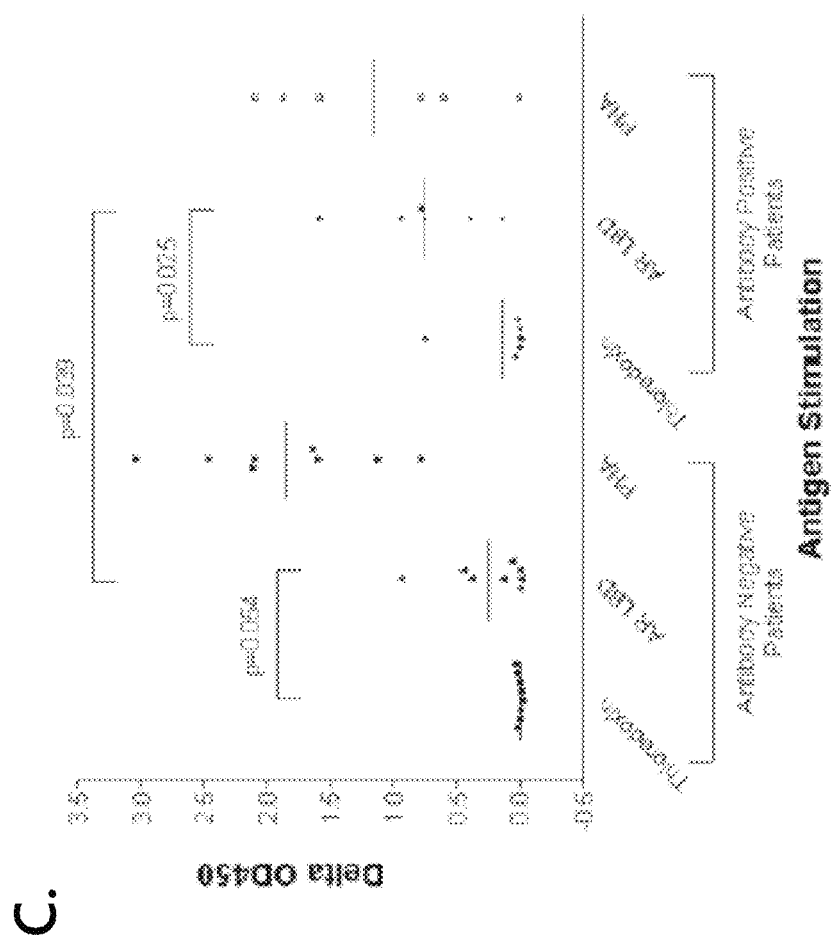
Figure 3:
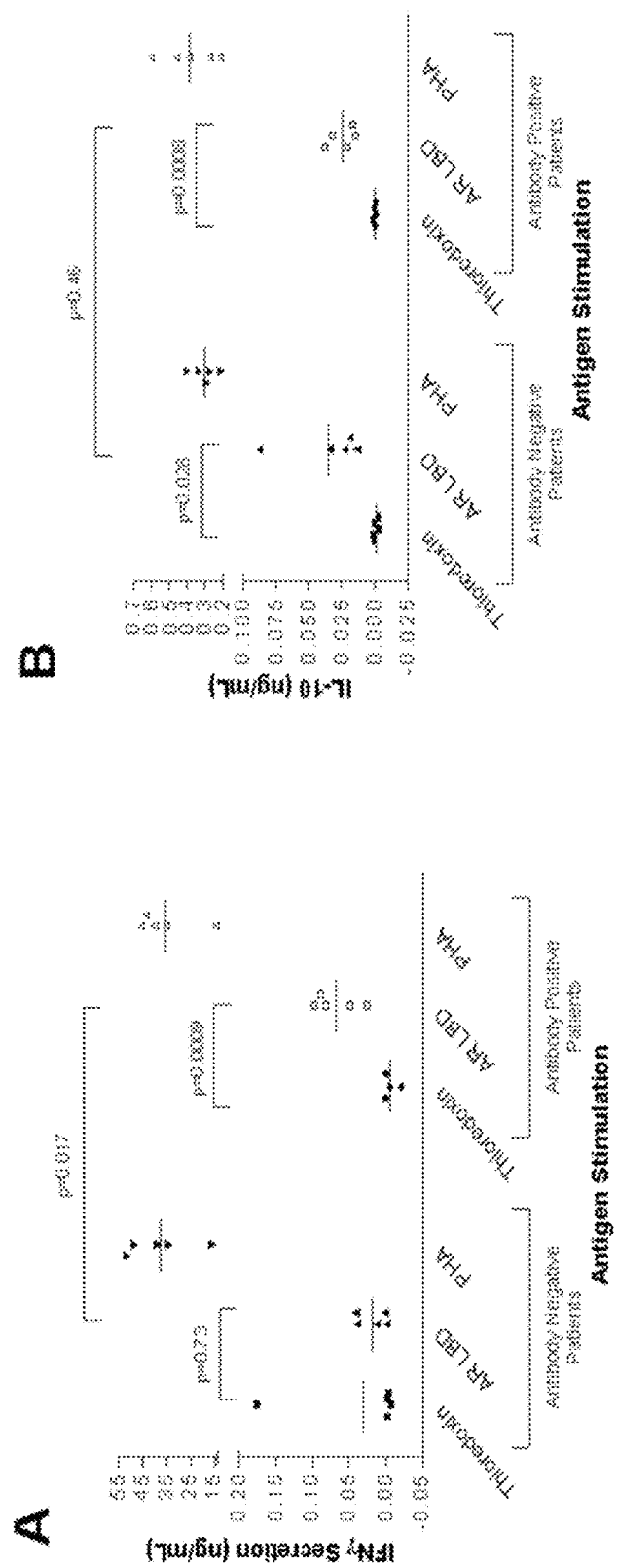
FIG. 3 shows that patients with AR LBD-specific IgG antibodies have a mixed Th1/Th2-type immune response. PBMC from prostate cancer patients with (n=5) or without (n=5) antibody responses specific for the AR were analyzed for the presence of antigen-specific IFNγ or IL-10-secretion. PBMC were stimulated with thioredoxin-tagged AR LBD, thioredoxin alone, media only, or PHA. After a 96-hour stimulation, supernatants were analyzed for the presence of IFNγ (panel A) and IL-10 (panel B) secretion by quantitative ELISA. A comparison of results among different antigen-stimulation conditions was performed using a Student's T test. The results shown are representative of duplicate experiments with the same peripheral blood samples.

Immune Responses to Androgen Receptor Ligand-Binding Domain can Exist in Patients with Prostate Cancer We evaluated whether or not patients with prostate cancer have existing immune responses to the androgen receptor (AR). We focused these studies on responses specific for the AR ligand-binding domain (LBD). As shown in FIG. 1, we found that prostate cancer patients, but not healthy male blood donors, have antibodies that are specific for the AR LBD. These antibodies were predominantly of the IgG isotype and $IgG_2$ sub-isotype (data not shown). Moreover, we identified that patients with antibody responses to the AR LBD have CD4+ and CD8+ T cells that proliferate, as well as cells that secrete interferon-gamma (IFNγ), in response to stimulation with the AR LBD (FIG. 2). Antigen-specific IL-10 secretion was observed in many patients who did not have evidence of antibody responses to AR LBD (FIG. 3). Taken together, these results demonstrate that some patients with prostate cancer can have pre-existing cellular immune responses specific for the AR. These findings further suggest that tolerance against the AR, which may be prevalent, is not absolute and can be overcome in some patients with prostate cancer.

Example 2

Materials and Methods

Subject Population:

Peripheral blood mononuclear cells (PBMC) were obtained from eleven patients with prostate cancer at the University of Wisconsin Hospital and Clinics between 2001 and 2007. All subjects gave Institutional Review Board-approved written informed consent for their blood products to be used for immunological research. PBMC were prepared from heparinized blood by gradient centrifugation.

T2 Binding Assay:

After passing T2 cells into fresh media the day before the assay, these cells were pulsed with 50 μg/mL peptide overnight at 37° C./5% $CO_2$. The next day, the levels of HLA-A2 expression on the surface of these cells were measured using a fluorescently-labeled HLA-A2 antibody (Clone BB7.2, BD Biosciences, San Jose, Calif.) followed by flow cytometry using FACSCaliber system (BD Biosciences). The reported "fold change" in fluorescence intensity was calculated by averaging the mean fluorescent intensity results from triplicate samples and dividing these values by the average mean fluorescent intensity of the negative control (media only) samples.

T-Cell Culturing:

Human prostate cancer patients underwent leukapheresis, and PBMCs were isolated using a Ficoll-Paque gradient (Pharmacia, Kirkland, Quebec). Immature dendritic cells (iDCs) were generated by incubating flask-adherent PBMCs with 20 ng/mL granulocyte-macrophage colony stimulating factor and 10 ng/mL interleukin four (IL-4) for six days at 37° C./5% $CO_2$ (cytokines from: Fitzgerald Industries, Concord, Mass.). These iDCs were then treated with 150 ng/mL IL-6, 10 ng/mL IL-1β, 10 ng/mL tumor necrosis factor alpha (TNF-α), and 1 mg/mL prostaglandin E2 (Fitzgerald Industries) to generate mature dendritic cells (mDCs). These mDCs were then pulsed with 20 μg/mL AR LBD-derived peptide, and after being irradiated were co-incubated with CD4+ and CD8+ T-cells negatively isolated from autologous PBMCs (Invitrogen, Carlsbad, Calif.). After incubating for 24 hours, these cultures were then treated with 10 U/mL IL-2 and 30 U/mL IL-7 (Fitzgerald Industries), and incubated for another 6 days. These cultured T-cells were re-stimulated weekly using peptide-pulsed antigen presenting cells (either mDCs or the TK6 lymphoma cell line).

Lactate Dehydrogenase Cytotoxicity Assay:

T-cell cultures that underwent at least two stimulations (or splenocyte cultures that had undergone one stimulation) were collected and incubated for four hours with target cells (either T2 cells pulsed for two hours with a specific or non-specific peptide, the LNCaP prostate cancer cell line, or media alone) at various effector-to-target ratios. After incubation, supernatants were collected and levels of lactate dehydrogenase were measured using the CytoTox 96 Non-Radioactive Assay (Promega). The relative percentage of peptide-specific lysis was quantitated using the following equation:

$$\% \text{ Cytotoxicity} = \frac{\text{Experimental} - \text{Effector Spontaneous} - \text{Target Spontaneous}}{\text{Target Maximum} - \text{Target Spontaneous}}$$

To conduct a mini-cytotoxicity assay of limited-dilution clones, 50 μl (¼) of the cultured clones were incubated for four hours with either T2 cells pulsed with the specific peptide, a non-specific peptide, or media alone. For the subsequent characterization of CTL clone cytotoxicity against prostate cancer cells, cryopreserved CTL clones were thawed, washed 3 times, and restimulated by incubating the clones with peptide-pulsed irradiated TK6 cells for 7 days. These clones were then resuspended in 10 U/mL IL-2, and allowed to incubate for three days at 37° C./5% $CO_2$. They were then analyzed for cytotoxicity (as described above) against four prostate cancer cell lines: LNCaP, DU145, LAPC4, and MDAPCa-2b cell lines. To characterize HLA-A2-restriction of observed cytotoxicity, a HLA-A2 antibody was added to the reaction (Clone BB7.2, BD Biosciences, 1 μg/mL).

Limited-Dilution T-Cell Cloning and T-Cell Expansion:

After T-cell cultures containing AR LBD peptide-specific T-cells were identified, peptide-specific T-cell clones were isolated using limited-dilution cloning. Briefly, cultured T-cells were diluted to 400 cells/mL, and were diluted at a 1:1 ratio down the rows of a 96-well plate. These T-cells were mixed with $2\times10^5$ autologous PBMCs, as well as an anti-CD3 antibody (Clone UCHT1, BD Biosciences, 120 ng/mL) and IL-2 (Fitzgerald Industries, 200 U/mL), and were incubated at 37° C./5% $CO_2$ for 12-14 days. Cultures generated from a single cell were identified, and their peptide-specificity was analyzed using a mini-cytotoxicity assay (as above). Peptide-specific T-cell clones were then expanded in the presence of autologous PBMCs, TK6 cells, and an anti-CD3 antibody (30 ng/mL). The next day, 50 U/mL IL-2 was added to the cultures. Six days later, CTL clones were resuspended in media with 80 U/mL IL2, and three days later were again resuspended in 20 U/mL IL-2. After three additional days, expanded T-cell clones were analyzed for cytotoxicity against peptide-specific or non-specific T2-pulsed cells (as described above).

Surface Molecule Staining:

T-cell clones were thawed, washed 3 times, and resuspended in media supplemented with 10 U/mL IL-2 for 18 hours at 37° C./5% $CO_2$. These recovered clones were then resuspended in staining buffer (phosphate-buffered saline+ 5% fetal bovine serum) and incubated with fluorescently-labeled antibodies specific for CD3, CD4, CD8, and CD56 (clones SK7, RPA-T4, RPA-T8, or NCAM16.2, respectively; BD Biosciences) or the appropriate controls, for 30 minutes on ice. Cells were subsequently analyzed using an LSR II flow cytometer (BD Biosciences), counting 100,000 events. Cells were gated based on CD3+/CD56+ expression and CD4+/CD8+ expression.

Intracellular Cytokine Staining:

Recovered CTL clones were restimulated for one hour with media alone, the specific peptide, a non-specific peptide (peptides both at 2 μg/mL), or Phorbol Myristate Acetate (Sigma-Aldrich, St. Louis, Mo.; 10 μg/mL) and Ionomycin (MP Biomedicals, Solon, Ohio; 1 μg/mL). Cells were then treated with monensin (BD Biosciences; 1 μl per 1.5 mL cell culture) for four hours at 37° C./5% $CO_2$, followed by a brief blocking treatment with mouse IgG. Cells were then resuspended in staining buffer (phosphate-buffered saline+5% fetal bovine serum) and incubated with fluorescently-labeled CD3- and CD8-specific antibodies (BD Biosciences), or the appropriate controls, for 30 minutes on ice. After fixation and permeabilization, intracellular staining was conducted using fluorescently-labeled IFNγ and TNFα antibodies (Clones 4S.B3 and MAb11, respectively; BD Biosciences), or the appropriate isotype controls. Cells were subsequently analyzed using an LSR II flow cytometer, counting 100,000 events. IFNγ and TNFα-positive events were determined by gating CD3+/CD8+ cells and analyzing this population for co-expression of IFNγ and TNFα.

Immunization of HLA-A2/HLA-DR1 Mice:

Groups of four 6-10 week old HLA-A2/DR1 transgenic male mice (Charles River Laboratory—France with the permission of Dr. François Lemmonier) were immunized subcutaneously with 100 μg AR811 peptide with Complete Freund's Adjuvant (CFA) or with CFA alone (Sigma-Aldrich), and seven days later, the mice were euthanized. Spleens were collected, and splenocytes were isolated by gradient centrifugation (Histopaque 3130, Sigma-Aldrich). Splenocytes were stimulated with 10 μg/mL peptide for two hours, and on the second day, recombinant murine IL-2 and IL-7 (Fitzgerald Industries) were added to 10 U/mL and 30 U/mL, respectively. The cultures were then allowed to incubate an additional six days before analysis.

Figure 4:
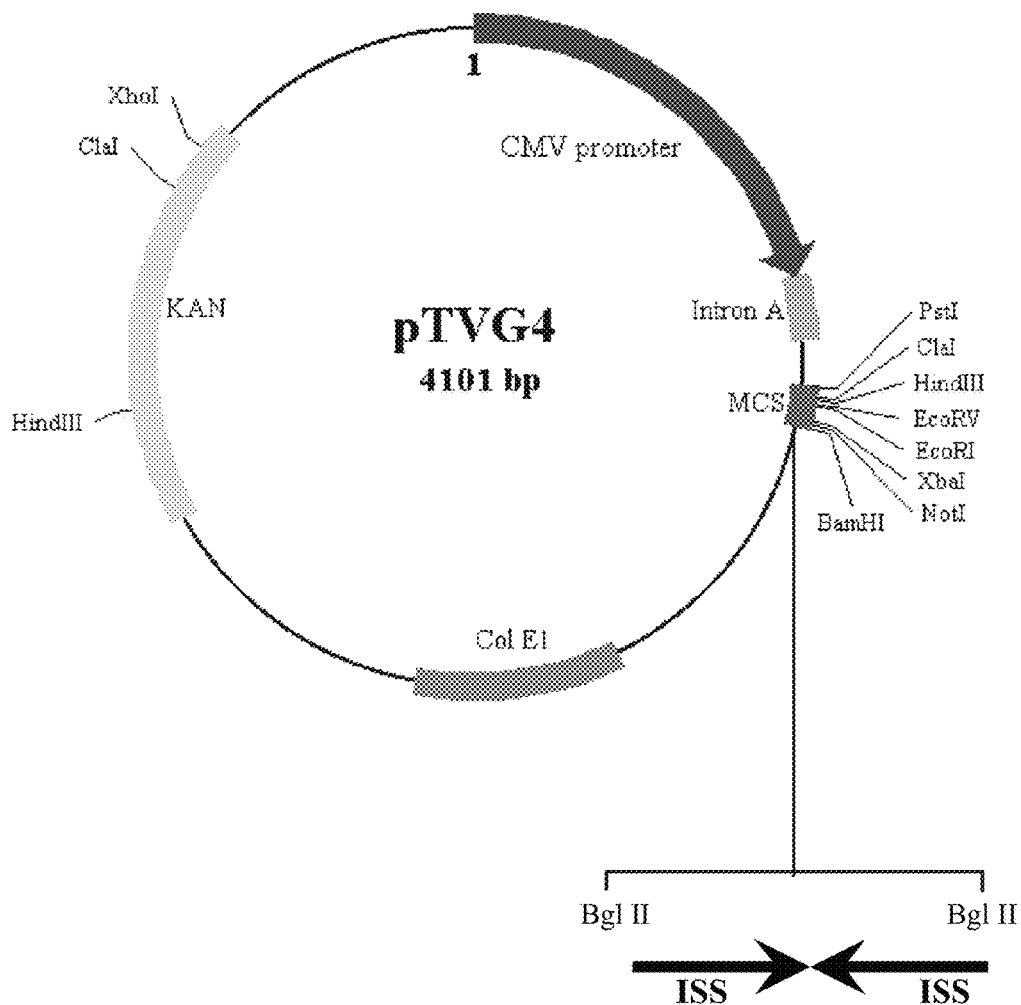
FIG. 4 shows the plasmid map of pTVG4.

Construction of pTVG4 and pTVG-ARLBD:

Plasmid DNA expression vectors have been developed for use in human vaccines. Shown in FIG. 4 is a plasmid map of the pTVG4 vector as constructed for animal (e.g., rat and mouse) and human immunization. The coding sequence for the ligand-binding domain of the human androgen receptor gene has been inserted into the pTVG4 vector to create the immunization vector pTVG-ARLBD (see below).

Figure 5:
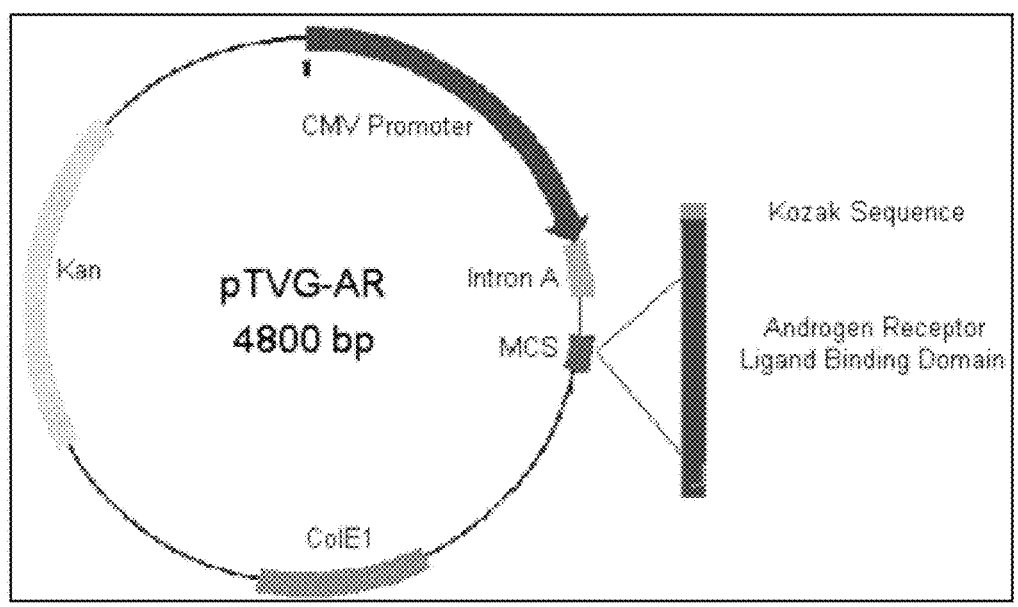
FIG. 5 shows the plasmid map of pTVG-ARLBD (pTVG-androgen receptor ligand-binding domain).

The plasmid vector pNGVL3 was obtained from the National Gene Vector Laboratory at the University of Michigan (courtesy, Dr. Robert Gerard). This vector, similar to the pCDNA3.1 expression vector from Invitrogen Corp. (Carlsbad, Calif.), drives transcription from the CMV promoter, but also includes the CMV intron A sequence to enhance transcription (Lee et al., 1997, Mol. Cells 7:495-501). The vector also contains a multi-cloning site, and does not express a eukaryotic antibiotic resistance gene, such that the only protein expression expected in a eukaryotic system is the one driven from the CMV promoter, unlike the pCDNA vector. To this vector has been added 2 copies of a 36-bp immunostimulatory (ISS) fragment containing the 5'-GTCGTT-3' motif previously identified (Hartmann et al., 2000, J. Immunol. 164:1617-24), to create the vector pTVG4 (FIG. 4). ColE1, the DNA sequence for Colicin E1 which can be used for cloning purpose, is provided in the vector. Kan, the DNA sequence encoding a kanamycin resistance gene which can also be used for cloning purpose, is also provided in the vector. The coding sequence for the ligand-binding domain of the human androgen receptor gene has been cloned into this vector and a Kozak sequence has been provided directly upstream of the coding sequence to enhance the translation of the corresponding mRNA (FIG. 5). Expression of the ligand-binding domain has been confirmed by in vitro expression studies (not shown). This construct, named pTVG-ARLBD, is used for the immunization of animals and humans.

Immunization and Tumor Protection of Copenhagen Rats:

Groups of ten 9-11 week old Copenhagen rats (Harlan) were immunized intradermally with 100 μg pTVG-ARLBD or 100 μg pTVG4 alone with 1 μg rat GM-CSF. Rats received three booster immunizations (100 μg) every 14 days, and 14 days after the last immunization, rats were challenged with 10,000 syngeneic Mat-LyLu prostate tumor cells, given along with Matrigel Matrix (BD Biosciences). Tumors (long and short diameters) were measured every two days, and volumes were calculated using the following equation:

$$\text{Tumor volume} = (\pi/6) \times (d_{short})^2 \times (d_{long})$$

Results

AR LBD-Specific CD8+ T-Cells from Prostate Cancer Patients can Lyse Prostate Cancer Cells:

To characterize CD8+ T-cell responses to the AR LBD, the amino acid sequence of the AR LBD was evaluated for potential HLA-A2-binding epitopes that fit the consensus peptide binding sequence of X-L/M-X-X-X-V-X-X-V/L (SEQ ID NO:8), using the algorithm of Parker and colleagues (Parker K C et al., 1994, J. Immunol. 152:163-175). As demonstrated in Table 1, ten unique peptides were identified. These peptides were synthesized and then characterized for their affinity for HLA-A2 in vitro using T2 binding assays. The results from these binding studies are also shown in Table 1. As demonstrated, several potential epitopes were predicted and found experimentally to bind strongly to HLA-A2. Peptide-specific T-cell lines were then cultured from the peripheral blood of 11 HLA-A2+ patients with prostate cancer, using each of these peptides, and then tested for their cytolytic activity against both peptide-pulsed HLA-A2-expressing target cells and the HLA-A2+ LNCaP prostate cancer cell line. Specifically, naive T cells were isolated by magnetic negative selection (Dynal) from the peripheral blood mononuclear cells (PBMCs) of HLA-A2-expressing prostate cancer patients, and cultured in the presence of autologous cytokine-matured irradiated dendritic cells (mDC) that had been loaded with individual peptides. These cultures received interleukin 2 (IL-2) and IL-7 the day after the culture, and were re-stimulated weekly with peptide-pulsed mDCs. Beginning after two weeks of stimulation, the T-cell cultures were tested weekly for their cytolytic activity using peptide-loaded T2 cells as target cells. Peptide-specific T-cells could be cultured from the majority of patients to at least one of these peptides, and peptide-specific T-cell lines could be cultured from the majority (7/11) of HLA-A2-expressing patients against the AR811 peptide in particular (Table 2).

TABLE 1

Prediction of AR LBD-derived HLA-A2-specific peptide epitopes.

| Peptide | Sequence | Predicted Binding Affinity ($t_{1/2}$ (min) of Dissociation) | In Vitro HLA-A2 Expression (Relative Mean Flourescent Intensity) |
|---|---|---|---|
| AR677 | VLEAIEPGV (SEQ ID NO: 13) | 7.6 | 1.37 ± 0.14 |
| AR700 | ALLSSLNEL (SEQ ID NO: 14) | 182 | 2.66 ± 0.28 |
| AR708 | LGERQLVHVV (SEQ ID NO: 15) | 0.114 | 1.16 ± 0.06 |
| AR742 | WMGLMVFAM (SEQ ID NO: 16) | 220 | 1.32 ± 0.06 |
| AR761 | RMLYFAPDLV (SEQ ID NO: 10) | 217 | 2.15 ± 0.13 |
| AR805 | FLCMKALLL (SEQ ID NO: 11) | 98 | 2.19 ± 0.14 |
| AR811 | LLLFSIIPV (SEQ ID NO: 9) | 1006 | 2.54 ± 0.25 |
| AR814 | FSIIPVDGL (SEQ ID NO: 17) | 111 | 1.01 ± 0.12 |
| AR859 | QLTKLLDSV (SEQ ID NO: 12) | 78 | 1.33 ± 0.15 |
| AR862 | KLLDSVQPI (SEQ ID NO: 18) | 1274 | 1.65 ± 0.19 |
| Influenza | GILGFVFTL (SEQ ID NO: 19) | 30 | 1.88 ± 0.24 |
| Negative Control | | 0 | 1.00 ± 0.07 |

AR LBD peptide epitopes were identified by scanning the protein sequence of the AR LBD for 9-mer or 10-mer peptides that fit the HLA-A2 consensus binding sequence X-L/M-X-X-X-V-X-X-V/L (SEQ ID NO: 8) and by their predicted binding affinity to HLA-A2 (Bioinformatics and Molecular Analysis Section). These peptides were synthesized and then analyzed for their affinity for HLA-A2 using a T2 binding assay.
Shown is the ratio of the mean fluorescent intensity, calculated from triplicate samples, of peptide-loaded T cells normalized against unloaded T cells.
Influenza: positive control influenza matrix protein peptide; negative control: vehicle.

TABLE 2

Compiled results of T cell culturing and cytotoxicity assays.

| Peptide | Peptide-specific lysis (Number of patients) | Prostate cancer cell lysis |
|---|---|---|
| AR677 | 2/11 | − |
| AR700 | 1/11 | − |
| AR708 | 1/11 | − |
| AR742 | 2/11 | − |
| AR761 | 6/11 | +/− |
| AR805 | 3/11 | +/− |
| AR811 | 7/11 | + |
| AR814 | 3/11 | − |
| AR859 | 2/11 | +/− |
| AR862 | 5/11 | − |

Shown in this table are the results obtained from cytotoxicity assays of T cell cultures from eleven HLA-A2-expressing patients with prostate cancer. In the second column is the number of patients for which peptide-specific T cells could be identified following 2-4 in vitro stimulations. The third column shows results as to whether those peptide-specific T cells were able to lyse the HLA-A2+ LNCaP prostate cancer cell line (+: positive lysis, −: no lysis, +/−: inconclusive).

Figure 6:
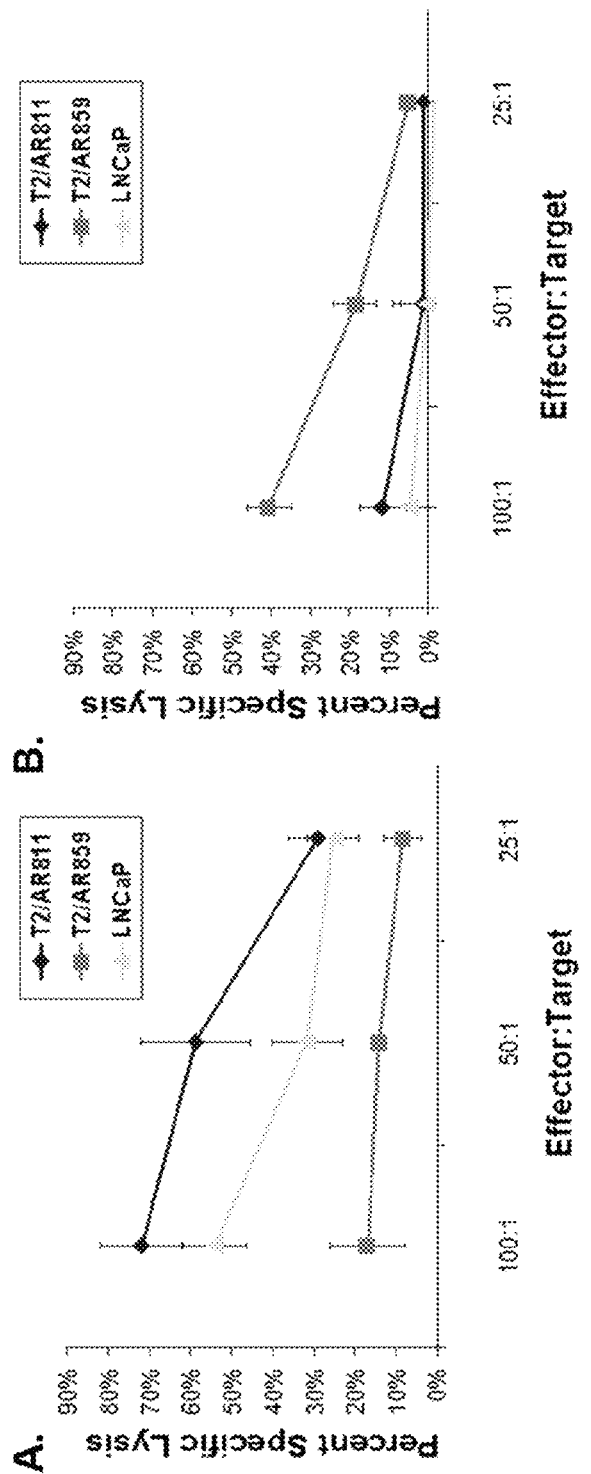
FIG. 6 shows that AR LBD peptide-specific T-cells can lyse peptide-pulsed and prostate cancer cell line target cells. Peptide-specific T-cell lines were cultured from the peripheral blood of HLA-A2-expressing patients with prostate cancer using peptides AR811 (LLLFSIIPV, SEQ ID NO:9, panel A) or AR859 (QLTKLLDSV, SEQ ID NO:12, panel B). After several in vitro restimulations, cultures were tested for cytolytic activity to T2 cells loaded with AR811 peptide (diamond), AR859 (square), or the LNCaP HLA-A2 expressing prostate cancer cell line (triangle). Shown is a representative graph results obtained from the cytotoxicity assay of T-cell cultures performed in triplicate at three different effector-to-target ratios as indicated.
Figure 7:
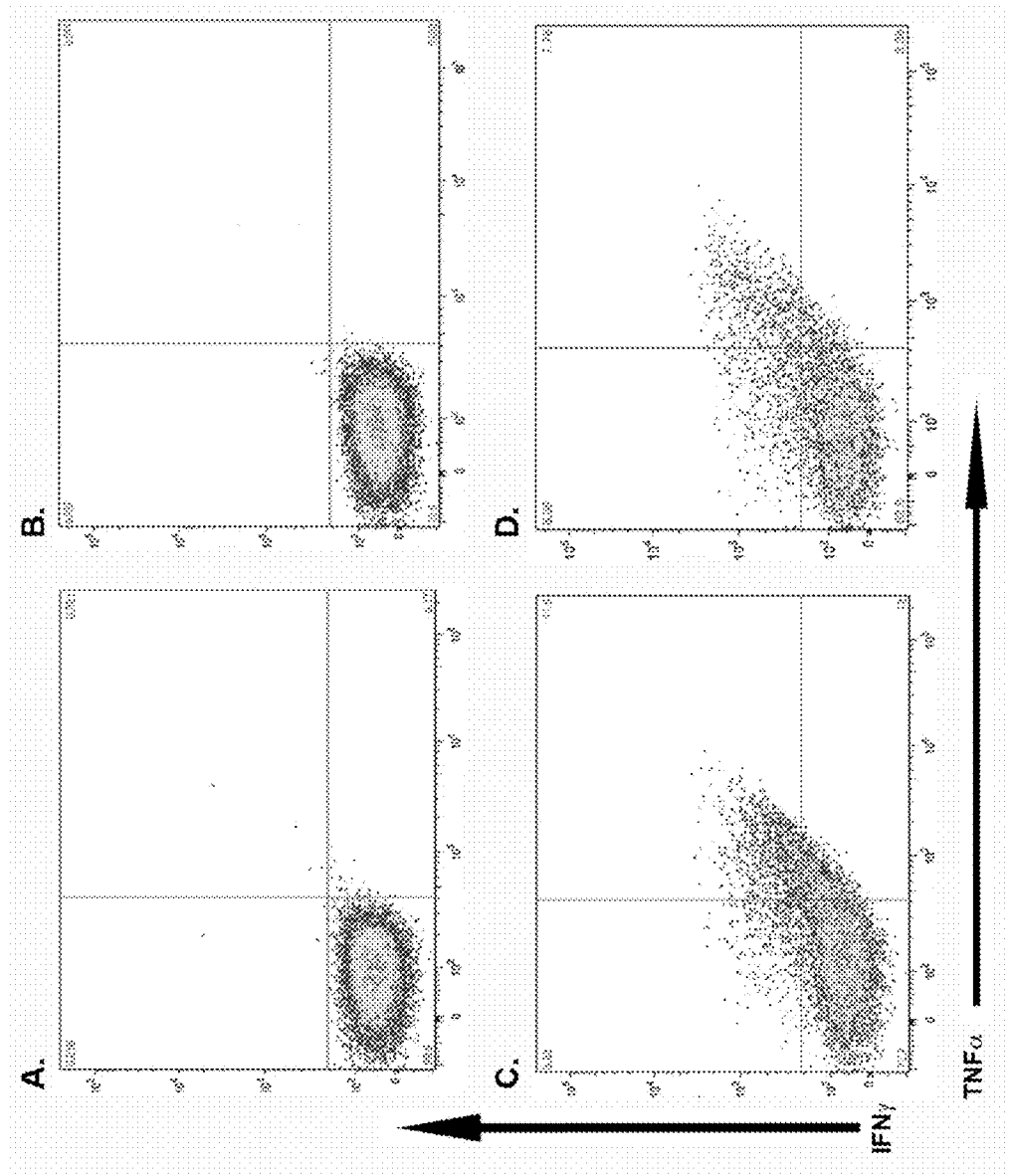
FIG. 7 shows that a T-cell clone specific for the AR811 peptide secretes IFNγ and TNFα in response to peptide stimulation. A clonal T-cell line specific for the AR811 peptide was derived by limited dilution following multiple restimulations in vitro. This line was restimulated for 5 hours in vitro with T2 cells and media only (panel A), an irrelevant peptide (panel B), AR811 peptide (panel C), or PMA/Ionomycin (panel D). IFNγ and TNFα cytokine accumulation were assessed by intracellular flow cytometric analysis (Cytofix/cytoperm kit, BD Pharmingen). Cells were first stained for CD3 and CD8 expression and CD3+/CD8+ cells were analyzed for IFNγ and TNFα expression. Shown are the plots gated on CD3+/CD8+ cells.
Figure 8:
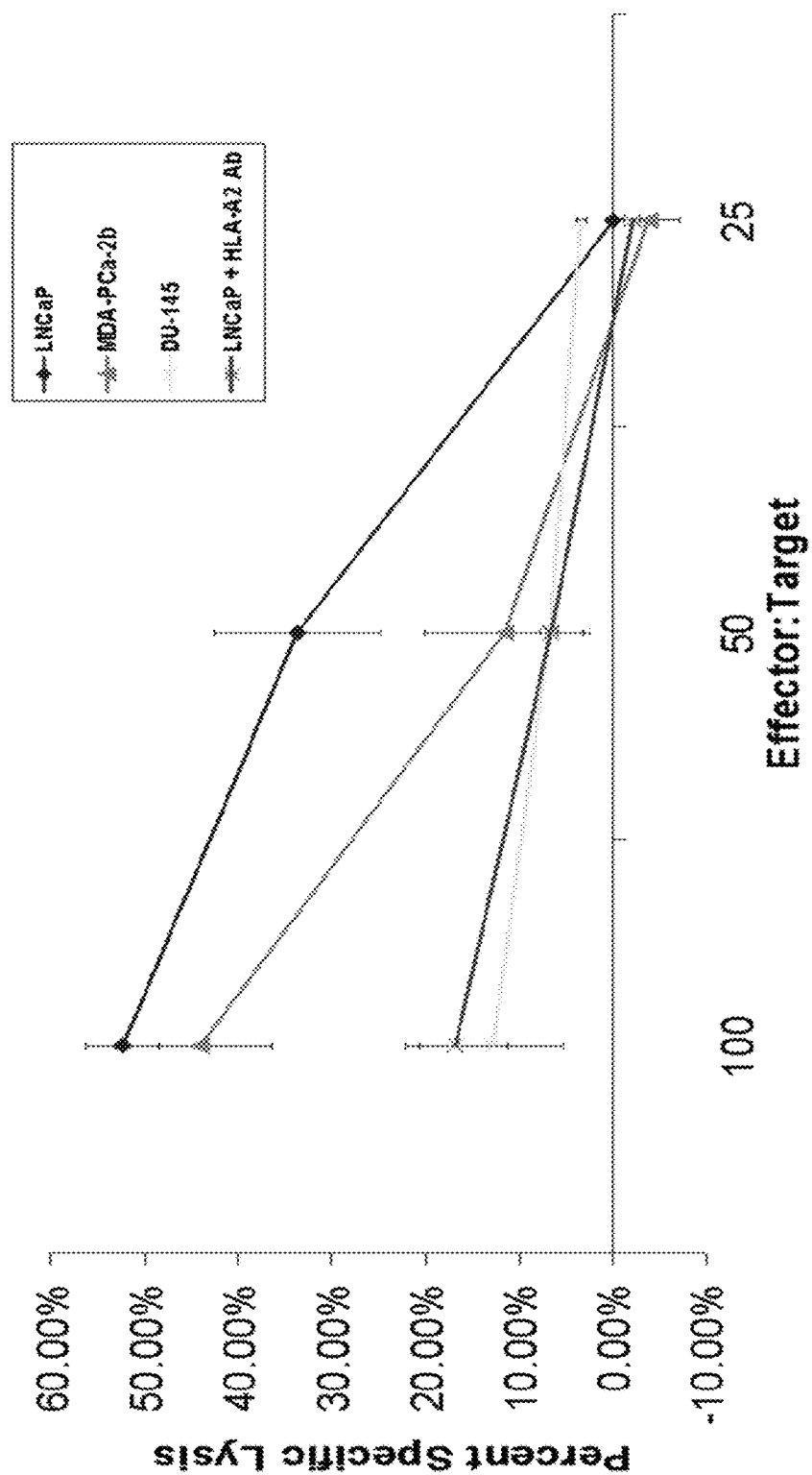
FIG. 8 shows that the AR811 epitope is a naturally processed HLA-A2-restricted T-cell epitope. The AR811 T-cell clone was tested for its ability to lyse prostate cancer cell lines (expressing the AR) that express HLA-A2 (LN-CaP, diamond and MDA-Pca-2B, triangle), or do not express HLA-A2 (DU145, X). In addition, lysis was evaluated following pre-treatment of LNCaP with an HLA-A2 blocking monoclonal antibody (starburst). Shown is a cytotoxicity assay of an AR811 CD8+ cell clone. Cells were restimulated for seven days using peptide-pulsed antigen presenting cells, followed on day seven by a rest period of three days before they were analyzed for their cytotoxic activity.

As shown in FIG. 6, AR811 peptide-specific T-cells were found to lyse T2 cells in a peptide-specific fashion, and could lyse the LNCaP cell line. Several other peptides demonstrated peptide-specific lysis and variable amounts of lysis against the LNCaP cell line (Table 2). In contrast, T-cells specific for the AR859 peptide could be cultured, and while these showed peptide-specific lysis they did not lyse the LNCaP cell line (FIG. 6B). AR811-specific T-cells were cloned by limited dilution and found to be CD8+, and to secrete both IFNγ and TNFα in response to peptide stimulation (FIG. 7). Moreover, these cells lysed prostate cancer cells in an MHC class I-restricted fashion (FIG. 8). These findings confirm that the AR811 peptide is a naturally processed and presented HLA-A2 epitope from the AR.

Figure 9:
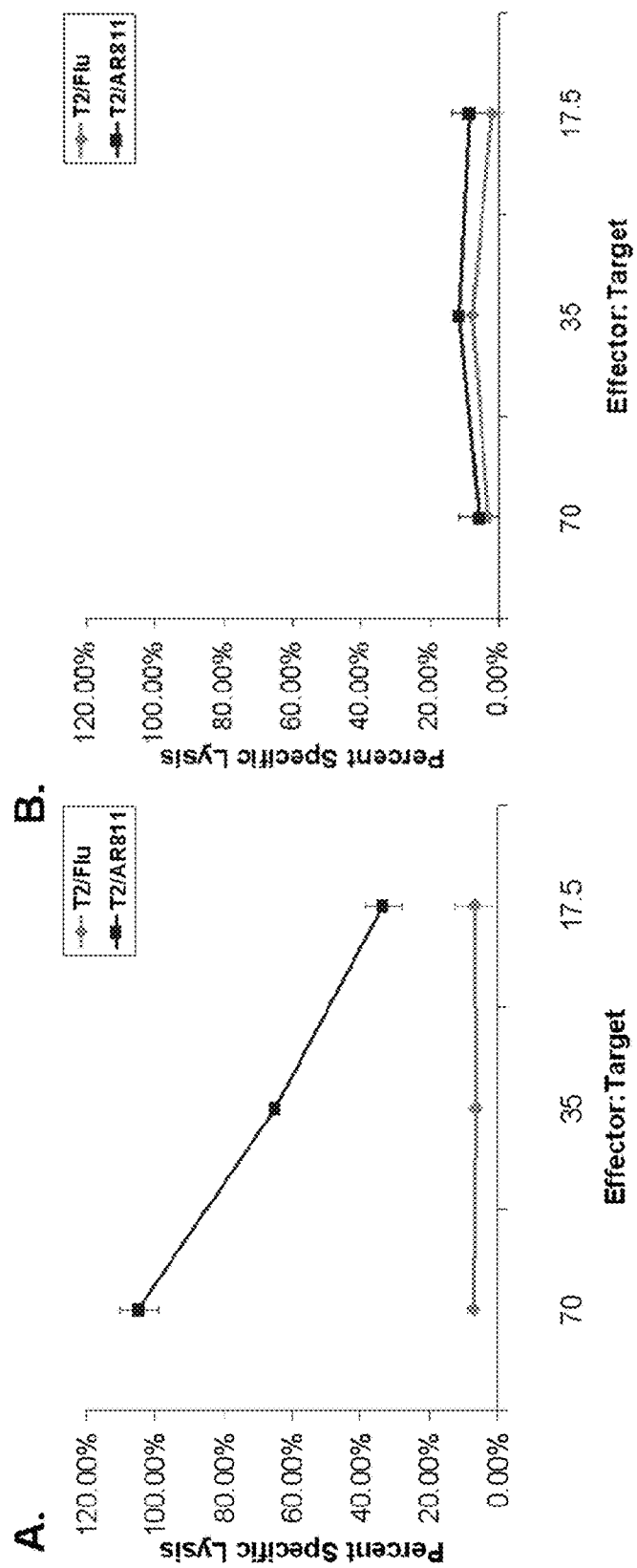
FIG. 9 shows that HHD-II mice immunized with AR811 peptide develop peptide-specific CTL (contain splenocytes that can specifically lyse AR811 target cells). Male HHD-II mice (n=3 per group) were immunized once with 100 μg AR811 peptide in CFA or with CFA alone. One week after immunization, splenocytes were collected and stimulated in vitro with 10 μg/mL peptide for two hours, and on the second day, recombinant murine IL-2 and IL-7 (Fitzgerald Industries) were added to 10 U/mL and 30 U/mL, respectively. The cultures were then allowed to incubate an additional six days before analysis. Cultured cells from from AR811-immunized animals (panel A) or control immunized animals (panel B) were then tested for cytolytic activity to T2 cells pulsed with the AR811 peptide (square) or T2 cells pulsed with an influenza matrix peptide (diamond). Shown are the mean and standard deviation of triplicate wells at three effector-to-target ratios as indicated, each from a single animal per group, and representative of the other animals per group.

HLA A2 Transgenic Mice Immunized with the AR811 Peptide Developed Peptide-Specific CTL:

Human HLA transgenic mice have become a valuable tool for the identification and study of human MHC class I-specific epitopes and CTL responses. In work published by others, transgenic mice expressing human HLA-A201 have been immunized directly with peptides, or with DNA encoding antigens, or protein antigens, to identify HLA-A2-specific epitopes (Carralot J P et al., 2005, Int Immunol 17:591-7; Gallez-Hawkins G et al., 2003, J Virol 77:4457-62; and Loirat D et al., 2000, J Immunol 165:4748-55). Unfortunately, many of the early studies with these transgenic strains were complicated by the preference to develop H-2-restricted murine responses rather than HLA-A2-restricted CTL responses, thus limiting the usefulness of these strains. This led to the development of the HHD strains by Dr. François Lemonnier and colleagues at the Institut Pasteur, in which the mouse MHC class I H-2Db was knocked out, and mice express human β2-microglobulin and HLA-A201 monochains fused to the α3, transmembrane and cytoplasmic domains of the mouse MHC class I molecule (Pascolo S et al., 1997, J Exp Med 185:2043-51). These strains and derivatives have been particularly useful as these mice are forced to use a diverse repertoire of CD8+ T-cells specific for HLA-A2 (Pascolo S et al., 1997, J Exp Med 185:2043-51), and have been demonstrated to be superior in eliciting HLA-A2-restricted CTL (Ramage J M et al., 2004, Vaccine 22:1728-31). The HHD-II transgenic mouse strain developed by Dr. Lemonnier expresses both human HLA-A0201 and HLA-DR1, and has both the murine H-2 class I and MHC class II knocked out (Pajot A et al., 2004, Eur J Immunol 34:3060-9). This particular strain has been used for the identification of HLA-DR1-restricted CD4+ T-cell epitopes as well as HLA-A2-restricted epitopes (Pajot A et al., 2006, Microbes Infect 8:2783-90). HHD-II mice were immunized once with 100 µg of the AR811 peptide in complete Freund's adjuvant (CFA) or with CFA alone. As shown in FIG. 9, AR811 peptide-specific CTL could be identified after immunization.

Figure 10:
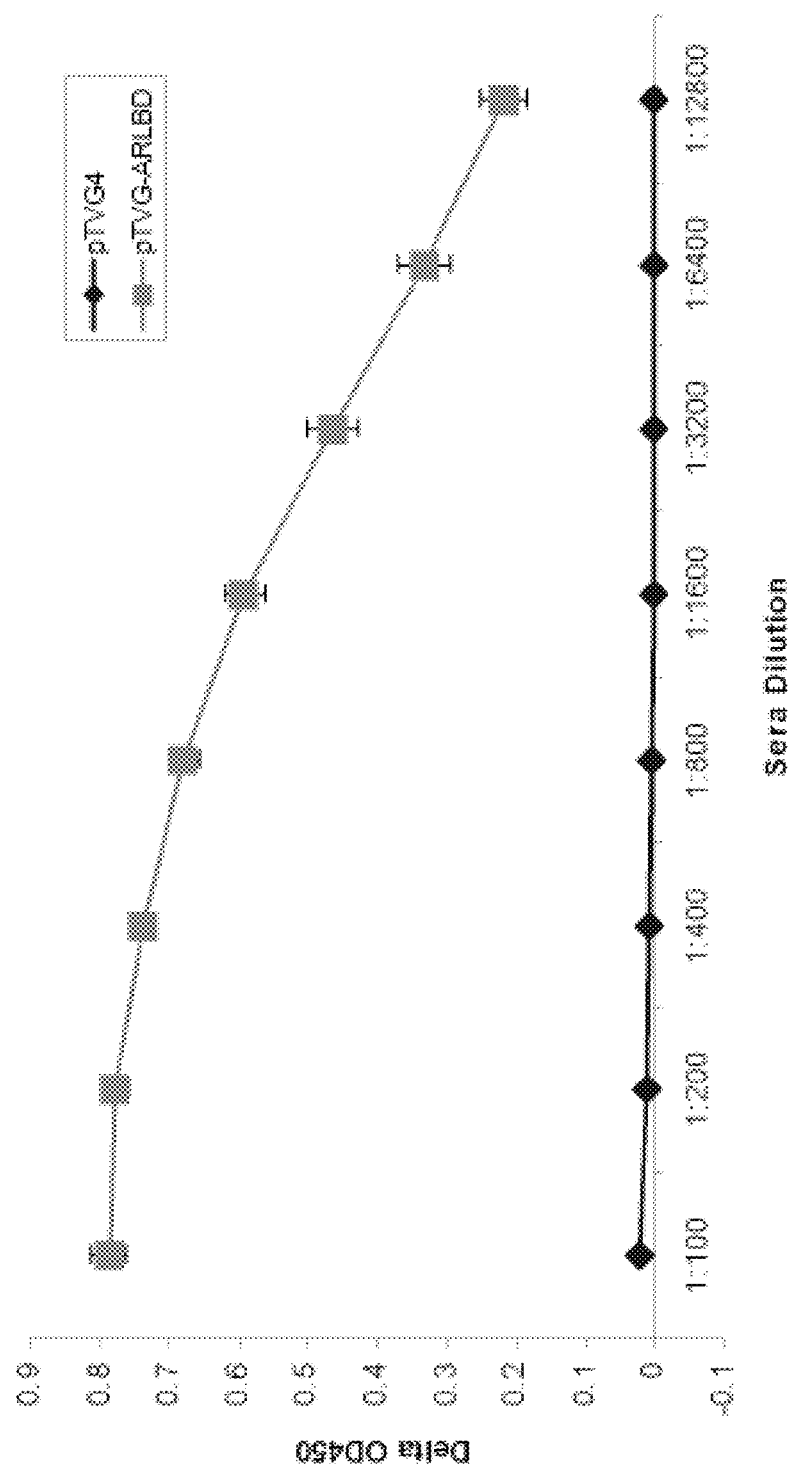
FIG. 10 shows that rats immunized with a plasmid vector encoding AR LBD develop AR LBD-specific antibody responses. Copenhagen rats were immunized 4 times at 14-day intervals with pTVG4 control vector or pTVG-ARLBD. Two weeks after the fourth immunization, blood was collected and assessed for antibody responses to the AR-LBD protein by ELISA. Shown are the mean and standard error for 10 animals per experimental group.
Figure 11:
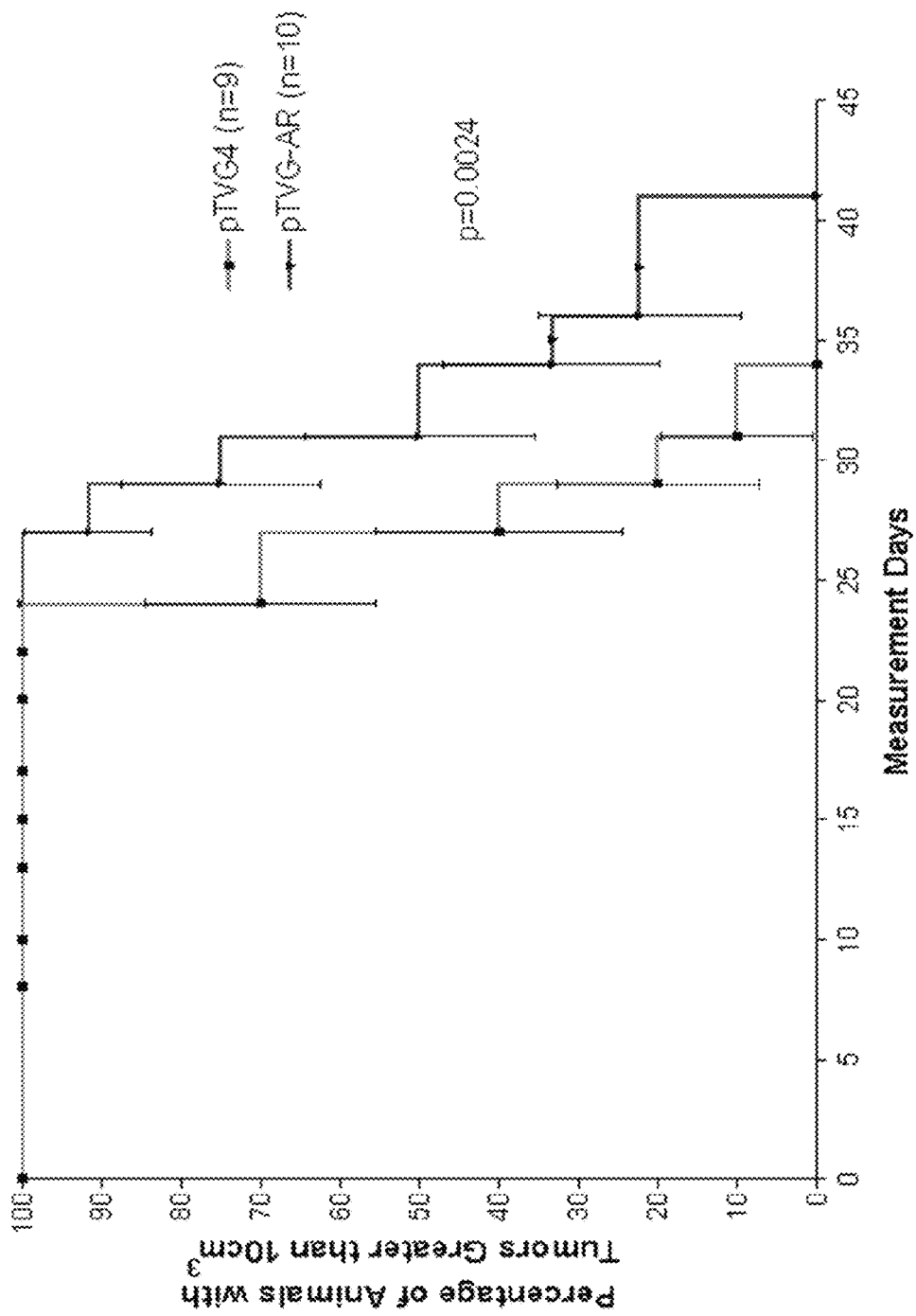
FIG. 11 shows tumor growth in pTVG4 control vector or pTVG-ARLBD immunized rats (Kaplan-Meier analysis of animal endpoint survival following treatment with the pTVG4 control vector or pTVG-ARLBD). Male Copenhagen rats were immunized four times every other week with pTVG4 control vector or pTVG-ARLBD. Two weeks after immunization, the rats were challenged with 1×10$^4$ syngeneic Mat-LyLu prostate cancer cells given with Matrigel. Tumors were measured every other day, and rats were sacrificed when tumors grew larger than 10 cm$^3$ (Kaplan-Meier survival end point being tumor volume over 10 cm$^3$).

DNA Vaccine Encoding AR LBD can Elicit Antigen-Specific Responses and Retard Prostate Cancer Cell Growth In Vivo:

cDNA was prepared from a prostate cancer cell line, and AR LBD (amino acids 664-920) was cloned into the pTVG4 vector as described above (similar to cloning prostatic acid phosphatase into the pTVG4 vector described in Johnson L E, et al., 2007, Canc Immunol Immunoth 56:885-895, which is herein incorporated by reference in its entirety). CHO cells transiently transfected with this pTVG-ARLBD construct produced AR LBD mRNA and protein that could be detected by RT-PCR and by Western blot analysis (data not shown). Male Copenhagen rats, 2-3 months of age, were then immunized with 100 µg of pTVG-ARLBD four times at 14-day intervals, intradermally with 5 µg rat GM-CSF given as a vaccine adjuvant. Two weeks after the final immunization, blood was collected for immunological analysis. As shown in FIG. 10, animals immunized with pTVG-ARLBD, but not the pTVG4 vector, developed AR LBD-specific IgG antibody responses. To assess anti-tumor efficacy, Copenhagen rats that had been immunized four times at 14-day intervals were then challenged with $1 \times 10^4$ syngeneic Mat-LyLu prostate tumor cells implanted subcutaneously. As shown in FIG. 11, immunization with pTVG-ARLBD, but not the pTVG4 vector, retarded the growth of these Mat-LyLu prostate tumors.

Example 3 (Prophetic)

Prostate Cancer Therapy with pTVG-ARLBD DNA Vaccine

Groups of ten suitable rats or mice such as Copenhagen rats are challenged with a suitable number of prostate cancer cells (e.g., $1 \times 10^4$ Mat-LyLu prostate cancer cells). These rats or mice are then immunized with either the pTVG4 (negative control) or pTVG-ARLBD constructs One example is to immunize the rats or mice at days 2, 9, and 16 after the tumor challenge with 100 µg injected intradermally along with 5 µg rat or mouse GM-CSF as an adjuvant. Suitable schemes with fewer or additional immunizations may be used as alternatives. Optionally, boosts (e.g., on weekly basis) can be provided. Other suitable amounts of DNA or adjuvant can be used, as can different adjuvants (such as Freund's adjuvant) or additional vaccines (such as those targeting prostatic acid phosphatase or the synovial sarcoma X chromosome family of proteins). In addition, other suitable routes of administration may be used (such as intravenously). Tumor growth is monitored daily using bi-dimensional measurements. Sera from these rats or mice may be obtained and used to evaluate the presence of AR LBD antibodies. It is expected that immunization with pTVG-ARLBD DNA vaccine will elicit therapeutic anti-tumor response.

The present invention is not intended to be limited to the foregoing examples, but encompasses all such modifications and variations as come within the scope of the appended claims.

We claim:

1. A method for inducing an immune reaction to androgen receptor in a mammal having prostate cancer, comprising administering to the mammal an effective amount of a polypeptide selected from the group consisting of (i) a mammalian androgen receptor (e.g., a human androgen receptor), (ii) a fragment of the androgen receptor that comprises the ligand-binding domain, (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12, whereby the mammal develops immune reaction against androgen receptor.

2. The method of claim 1, wherein the mammal is a human.

3. The method of claim 1, wherein the polypeptide is administered in a pharmaceutically acceptable carrier.

4. The method of claim 1, wherein the polypeptide is administered to the mammal intradermally, intramuscularly, intravascularly, or subcutaneously.

5. The method of claim 1, wherein both a humoral and cellular immune reactions against the androgen receptor are induced.

6. The method of claim 1, wherein the method comprises administering to the mammal an effective amount of the combination of (iii) a fragment of the ligand-binding domain defined by SEQ ID NO:9 and (iv) a fragment of the ligand-binding domain defined by SEQ ID NO:10.

7. The method of claim 1, wherein the method comprises administering to the mammal an effective amount of the combination of (iii) a fragment of the ligand-binding domain defined by SEQ ID NO:9, (iv) a fragment of the ligand-binding domain defined by SEQ ID NO:10, and (v) a fragment of the ligand-binding domain defined by SEQ ID NO:11.

8. The method of claim 1, wherein the method comprises administering to the mammal an effective amount of the combination of (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12, whereby the mammal develops immune reaction against androgen receptor.

* * * * *

SEQUENCE LISTING

<160> NUMBER OF SEQ ID NOS: 19

<210> SEQ ID NO 1
<211> LENGTH: 4314
<212> TYPE: DNA
<213> ORGANISM: Homo sapiens
<220> FEATURE:
<221> NAME/KEY: CDS
<222> LOCATION: (1116)..(3878)

<400> SEQUENCE: 1

```
cgagatcccg gggagccagc ttgctgggag agcgggacgg tccggagcaa gcccagaggc      60
agaggaggcg acagagggaa aaagggccga gctagccgct ccagtgctgt acaggagccg     120
aagggacgca ccacgccagc cccagcccgg ctccagcgac agccaacgcc tcttgcagcg     180
cggcggcttc gaagccgccg cccggagctg ccctttcctc ttcggtgaag ttttaaaag      240 ctgctaaaga ctcggaggaa gcaaggaaag tgcctggtag gactgacggc tgcctttgtc     300
ctcctcctct ccaccccgcc tcccccacc  ctgccttccc ccctccccc  gtcttctctc     360 ccgcagctgc ctcagtcggc tactctcagc caaccccct  caccacccctt ctccccaccc    420 gccccccgc  cccgtcggc  ccagcgctgc cagcccgagt ttgcagagag gtaactccct     480
ttggctgcga gcgggcgagc tagctgcaca ttgcaaagaa ggctcttagg agccaggcga     540
ctggggagcg gcttcagcac tgcagccacg acccgcctgg ttaggctgca cgcggagaga     600
accctctgtt ttccccccact ctctctccac ctcctcctgc cttccccacc ccgagtgcgg    660
agccagagat caaaagatga aaaggcagtc aggtcttcag tagccaaaaa acaaaacaaa     720
caaaaacaaa aaagccgaaa taaagaaaa  agataataac tcagttctta tttgcaccta     780
cttcagtgga cactgaattt ggaaggtgga ggattttgtt ttttctttt  aagatctggg     840 catcttttga atctaccctt caagtattaa gagacagact gtgagcctag caggcagat      900 cttgtccacc gtgtgtcttc ttctgcacga actttgagg  ctgtcagagc gcttttgcg      960 tggttgctcc cgcaagtttc cttctctgga gcttcccgca ggtgggcagc tagctgcagc    1020
gactaccgca tcatcacagc ctgttgaact cttctgagca agaaggggg  aggcggggta    1080 agggaagtag gtggaagatt cagccaagct caagg atg gaa gtg cag tta ggg       1133
                                       Met Glu Val Gln Leu Gly
                                         1               5
```

```
ctg gga agg gtc tac cct cgg ccg ccg tcc aag acc tac cga gga gct      1181
Leu Gly Arg Val Tyr Pro Arg Pro Pro Ser Lys Thr Tyr Arg Gly Ala
           10                  15                  20
```

```
ttc cag aat ctg ttc cag agc gtg cgc gaa gtg atc cag aac ccg ggc      1229
Phe Gln Asn Leu Phe Gln Ser Val Arg Glu Val Ile Gln Asn Pro Gly
       25                  30                  35
```

```
ccc agg cac cca gag gcc gcg agc gca gca cct ccc ggc gcc agt ttg      1277
Pro Arg His Pro Glu Ala Ala Ser Ala Ala Pro Pro Gly Ala Ser Leu
   40                  45                  50
```

```
ctg ctg ctg cag cag cag cag cag cag cag cag cag cag cag cag cag      1325
Leu Leu Leu Gln Gln Gln Gln Gln Gln Gln Gln Gln Gln Gln Gln Gln
55                  60                  65                  70
```

```
cag cag cag cag cag cag cag cag caa gag act agc ccc agg cag          1373
Gln Gln Gln Gln Gln Gln Gln Gln Gln Glu Thr Ser Pro Arg Gln
               75                  80                  85
```

```
cag cag cag cag cag ggt gag gat ggt tct ccc caa gcc cat cgt aga      1421
Gln Gln Gln Gln Gln Gly Glu Asp Gly Ser Pro Gln Ala His Arg Arg
           90                  95                 100
```

```
ggc ccc aca ggc tac ctg gtc ctg gat gag gaa cag caa cct tca cag      1469
Gly Pro Thr Gly Tyr Leu Val Leu Asp Glu Glu Gln Gln Pro Ser Gln
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 105 |     |     |     |     | 110 |     |     |     |     | 115 |     |     |      |
| ccg | cag | tcg | gcc | ctg | gag | tgc | cac | ccc | gag | aga | ggt | tgc | gtc | cca | gag | 1517 |
| Pro | Gln | Ser | Ala | Leu | Glu | Cys | His | Pro | Glu | Arg | Gly | Cys | Val | Pro | Glu |      |
|     | 120 |     |     |     | 125 |     |     |     |     | 130 |     |     |     |     |     |      |
| cct | gga | gcc | gcc | gtg | gcc | gcc | agc | aag | ggg | ctg | ccg | cag | cag | ctg | cca | 1565 |
| Pro | Gly | Ala | Ala | Val | Ala | Ala | Ser | Lys | Gly | Leu | Pro | Gln | Gln | Leu | Pro |      |
| 135 |     |     |     |     | 140 |     |     |     |     | 145 |     |     |     |     | 150 |      |
| gca | cct | ccg | gac | gag | gat | gac | tca | gct | gcc | cca | tcc | acg | ttg | tcc | ctg | 1613 |
| Ala | Pro | Pro | Asp | Glu | Asp | Asp | Ser | Ala | Ala | Pro | Ser | Thr | Leu | Ser | Leu |      |
|     |     |     |     |     | 155 |     |     |     |     | 160 |     |     |     |     | 165 |      |
| ctg | ggc | ccc | act | ttc | ccc | ggc | tta | agc | agc | tgc | tcc | gct | gac | ctt | aaa | 1661 |
| Leu | Gly | Pro | Thr | Phe | Pro | Gly | Leu | Ser | Ser | Cys | Ser | Ala | Asp | Leu | Lys |      |
|     |     |     | 170 |     |     |     |     | 175 |     |     |     |     | 180 |     |     |      |
| gac | atc | ctg | agc | gag | gcc | agc | acc | atg | caa | ctc | ctt | cag | caa | cag | cag | 1709 |
| Asp | Ile | Leu | Ser | Glu | Ala | Ser | Thr | Met | Gln | Leu | Leu | Gln | Gln | Gln | Gln |      |
|     |     |     |     | 185 |     |     |     |     | 190 |     |     |     |     | 195 |     |      |
| cag | gaa | gca | gta | tcc | gaa | ggc | agc | agc | agc | ggg | aga | gcg | agg | gag | gcc | 1757 |
| Gln | Glu | Ala | Val | Ser | Glu | Gly | Ser | Ser | Ser | Gly | Arg | Ala | Arg | Glu | Ala |      |
|     | 200 |     |     |     |     | 205 |     |     |     |     | 210 |     |     |     |     |      |
| tcg | ggg | gct | ccc | act | tcc | tcc | aag | gac | aat | tac | tta | ggg | ggc | act | tcg | 1805 |
| Ser | Gly | Ala | Pro | Thr | Ser | Ser | Lys | Asp | Asn | Tyr | Leu | Gly | Gly | Thr | Ser |      |
| 215 |     |     |     |     | 220 |     |     |     |     | 225 |     |     |     |     | 230 |      |
| acc | att | tct | gac | aac | gcc | aag | gag | ttg | tgt | aag | gca | gtg | tcg | gtg | tcc | 1853 |
| Thr | Ile | Ser | Asp | Asn | Ala | Lys | Glu | Leu | Cys | Lys | Ala | Val | Ser | Val | Ser |      |
|     |     |     |     | 235 |     |     |     |     | 240 |     |     |     |     | 245 |     |      |
| atg | ggc | ctg | ggt | gtg | gag | gcg | ttg | gag | cat | ctg | agt | cca | ggg | gaa | cag | 1901 |
| Met | Gly | Leu | Gly | Val | Glu | Ala | Leu | Glu | His | Leu | Ser | Pro | Gly | Glu | Gln |      |
|     |     | 250 |     |     |     |     | 255 |     |     |     |     | 260 |     |     |     |      |
| ctt | cgg | ggg | gat | tgc | atg | tac | gcc | cca | ctt | ttg | gga | gtt | cca | ccc | gct | 1949 |
| Leu | Arg | Gly | Asp | Cys | Met | Tyr | Ala | Pro | Leu | Leu | Gly | Val | Pro | Pro | Ala |      |
|     |     | 265 |     |     |     |     | 270 |     |     |     |     | 275 |     |     |     |      |
| gtg | cgt | ccc | act | cct | tgt | gcc | cca | ttg | gcc | gaa | tgc | aaa | ggt | tct | ctg | 1997 |
| Val | Arg | Pro | Thr | Pro | Cys | Ala | Pro | Leu | Ala | Glu | Cys | Lys | Gly | Ser | Leu |      |
|     | 280 |     |     |     |     | 285 |     |     |     |     | 290 |     |     |     |     |      |
| cta | gac | gac | agc | gca | ggc | aag | agc | act | gaa | gat | act | gct | gag | tat | tcc | 2045 |
| Leu | Asp | Asp | Ser | Ala | Gly | Lys | Ser | Thr | Glu | Asp | Thr | Ala | Glu | Tyr | Ser |      |
| 295 |     |     |     |     | 300 |     |     |     |     | 305 |     |     |     |     | 310 |      |
| cct | ttc | aag | gga | ggt | tac | acc | aaa | ggg | cta | gaa | ggc | gag | agc | cta | ggc | 2093 |
| Pro | Phe | Lys | Gly | Gly | Tyr | Thr | Lys | Gly | Leu | Glu | Gly | Glu | Ser | Leu | Gly |      |
|     |     |     |     | 315 |     |     |     |     | 320 |     |     |     |     | 325 |     |      |
| tgc | tct | ggc | agc | gct | gca | gca | ggg | agc | tcc | ggg | aca | ctt | gaa | ctg | ccg | 2141 |
| Cys | Ser | Gly | Ser | Ala | Ala | Ala | Gly | Ser | Ser | Gly | Thr | Leu | Glu | Leu | Pro |      |
|     |     |     | 330 |     |     |     |     | 335 |     |     |     |     | 340 |     |     |      |
| tct | acc | ctg | tct | ctc | tac | aag | tcc | gga | gca | ctg | gac | gag | gca | gct | gcg | 2189 |
| Ser | Thr | Leu | Ser | Leu | Tyr | Lys | Ser | Gly | Ala | Leu | Asp | Glu | Ala | Ala | Ala |      |
|     |     | 345 |     |     |     |     | 350 |     |     |     |     | 355 |     |     |     |      |
| tac | cag | agt | cgc | gac | tac | tac | aac | ttt | cca | ctg | gct | ctg | gcc | gga | ccg | 2237 |
| Tyr | Gln | Ser | Arg | Asp | Tyr | Tyr | Asn | Phe | Pro | Leu | Ala | Leu | Ala | Gly | Pro |      |
|     | 360 |     |     |     | 365 |     |     |     |     | 370 |     |     |     |     |     |      |
| ccg | ccc | cct | ccg | ccg | cct | ccc | cat | ccc | cac | gct | cgc | atc | aag | ctg | gag | 2285 |
| Pro | Pro | Pro | Pro | Pro | Pro | His | Pro | His | Ala | Arg | Ile | Lys | Leu | Glu |     |      |
| 375 |     |     |     |     | 380 |     |     |     |     | 385 |     |     |     |     | 390 |      |
| aac | ccg | ctg | gac | tac | ggc | agc | gcc | tgg | gcg | gct | gcg | gcg | gcg | cag | tgc | 2333 |
| Asn | Pro | Leu | Asp | Tyr | Gly | Ser | Ala | Trp | Ala | Ala | Ala | Ala | Ala | Gln | Cys |      |
|     |     |     |     | 395 |     |     |     |     | 400 |     |     |     |     | 405 |     |      |
| cgc | tat | ggg | gac | ctg | gcg | agc | ctg | cat | ggc | gcg | ggt | gca | gcg | gga | ccc | 2381 |
| Arg | Tyr | Gly | Asp | Leu | Ala | Ser | Leu | His | Gly | Ala | Gly | Ala | Ala | Gly | Pro |      |
|     |     |     | 410 |     |     |     |     | 415 |     |     |     |     | 420 |     |     |      |
| ggt | tct | ggg | tca | ccc | tca | gcc | gcc | gct | tcc | tca | tcc | tgg | cac | act | ctc | 2429 |

```
Gly Ser Gly Ser Pro Ser Ala Ala Ser Ser Ser Trp His Thr Leu
        425             430             435 ttc aca gcc gaa gaa ggc cag ttg tat gga ccg tgt ggt ggt ggg       2477
Phe Thr Ala Glu Glu Gly Gln Leu Tyr Gly Pro Cys Gly Gly Gly
        440             445             450 ggt ggt ggc ggc ggc ggc ggc ggc ggc ggc ggc ggc ggc ggc ggc       2525
Gly Gly Gly Gly Gly Gly Gly Gly Gly Gly Gly Gly Gly Gly Gly
455             460             465             470 ggc ggc ggc gag gcg gga gct gta gcc ccc tac ggc tac act cgg ccc   2573
Gly Gly Gly Glu Ala Gly Ala Val Ala Pro Tyr Gly Tyr Thr Arg Pro
                475             480             485 cct cag ggg ctg gcg ggc cag gaa agc gac ttc acc gca cct gat gtg   2621
Pro Gln Gly Leu Ala Gly Gln Glu Ser Asp Phe Thr Ala Pro Asp Val
        490             495             500 tgg tac cct ggc ggc atg gtg agc aga gtg ccc tat ccc agt ccc act   2669
Trp Tyr Pro Gly Gly Met Val Ser Arg Val Pro Tyr Pro Ser Pro Thr
        505             510             515 tgt gtc aaa agc gaa atg ggc ccc tgg atg gat agc tac tcc gga cct   2717
Cys Val Lys Ser Glu Met Gly Pro Trp Met Asp Ser Tyr Ser Gly Pro
        520             525             530 tac ggg gac atg cgt ttg gag act gcc agg gac cat gtt ttg ccc att   2765
Tyr Gly Asp Met Arg Leu Glu Thr Ala Arg Asp His Val Leu Pro Ile
535             540             545             550 gac tat tac ttt cca ccc cag aag acc tgc ctg atc tgt gga gat gaa   2813
Asp Tyr Tyr Phe Pro Pro Gln Lys Thr Cys Leu Ile Cys Gly Asp Glu
                555             560             565 gct tct ggg tgt cac tat gga gct ctc aca tgt gga agc tgc aag gtc   2861
Ala Ser Gly Cys His Tyr Gly Ala Leu Thr Cys Gly Ser Cys Lys Val
        570             575             580 ttc ttc aaa aga gcc gct gaa ggg aaa cag aag tac ctg tgc gcc agc   2909
Phe Phe Lys Arg Ala Ala Glu Gly Lys Gln Lys Tyr Leu Cys Ala Ser
        585             590             595 aga aat gat tgc act att gat aaa ttc cga agg aaa aat tgt cca tct   2957
Arg Asn Asp Cys Thr Ile Asp Lys Phe Arg Arg Lys Asn Cys Pro Ser
600             605             610 tgt cgt ctt cgg aaa tgt tat gaa gca ggg atg act ctg gga gcc cgg   3005
Cys Arg Leu Arg Lys Cys Tyr Glu Ala Gly Met Thr Leu Gly Ala Arg
615             620             625             630 aag ctg aag aaa ctt ggt aat ctg aaa cta cag gag gaa gga gag gct   3053
Lys Leu Lys Lys Leu Gly Asn Leu Lys Leu Gln Glu Glu Gly Glu Ala
                635             640             645 tcc agc acc acc agc ccc act gag gag aca acc cag aag ctg aca gtg   3101
Ser Ser Thr Thr Ser Pro Thr Glu Glu Thr Thr Gln Lys Leu Thr Val
        650             655             660 tca cac att gaa ggc tat gaa tgt cag ccc atc ttt ctg aat gtc ctg   3149
Ser His Ile Glu Gly Tyr Glu Cys Gln Pro Ile Phe Leu Asn Val Leu
        665             670             675 gaa gcc att gag cca ggt gta gtg tgt gct gga cac gac aac aac cag   3197
Glu Ala Ile Glu Pro Gly Val Val Cys Ala Gly His Asp Asn Asn Gln
680             685             690 ccc gac tcc ttt gca gcc ttg ctc tct agc ctc aat gaa ctg gga gag   3245
Pro Asp Ser Phe Ala Ala Leu Leu Ser Ser Leu Asn Glu Leu Gly Glu
695             700             705             710 aga cag ctt gta cac gtg gtc aag tgg gcc aag gcc ttg cct ggc ttc   3293
Arg Gln Leu Val His Val Val Lys Trp Ala Lys Ala Leu Pro Gly Phe
                715             720             725 cgc aac tta cac gtg gac gac cag atg gct gtc att cag tac tcc tgg   3341
Arg Asn Leu His Val Asp Asp Gln Met Ala Val Ile Gln Tyr Ser Trp
        730             735             740
```

| | | |
|---|---|---|
| atg ggg ctc atg gtg ttt gcc atg ggc tgg cga tcc ttc acc aat gtc<br>Met Gly Leu Met Val Phe Ala Met Gly Trp Arg Ser Phe Thr Asn Val<br>                745                    750                        755 | | 3389 |
| aac tcc agg atg ctc tac ttc gcc cct gat ctg gtt ttc aat gag tac<br>Asn Ser Arg Met Leu Tyr Phe Ala Pro Asp Leu Val Phe Asn Glu Tyr<br>760                          765                    770 | | 3437 |
| cgc atg cac aag tcc cgg atg tac agc cag tgt gtc cga atg agg cac<br>Arg Met His Lys Ser Arg Met Tyr Ser Gln Cys Val Arg Met Arg His<br>775                        780                    785                    790 | | 3485 |
| ctc tct caa gag ttt gga tgg ctc caa atc acc ccc cag gaa ttc ctg<br>Leu Ser Gln Glu Phe Gly Trp Leu Gln Ile Thr Pro Gln Glu Phe Leu<br>                795                    800                    805 | | 3533 |
| tgc atg aaa gca ctg cta ctc ttc agc att att cca gtg gat ggg ctg<br>Cys Met Lys Ala Leu Leu Leu Phe Ser Ile Ile Pro Val Asp Gly Leu<br>810                          815                    820 | | 3581 |
| aaa aat caa aaa ttc ttt gat gaa ctt cga atg aac tac atc aag gaa<br>Lys Asn Gln Lys Phe Phe Asp Glu Leu Arg Met Asn Tyr Ile Lys Glu<br>                825                    830                    835 | | 3629 |
| ctc gat cgt atc att gca tgc aaa aga aaa aat ccc aca tcc tgc tca<br>Leu Asp Arg Ile Ile Ala Cys Lys Arg Lys Asn Pro Thr Ser Cys Ser<br>840                          845                    850 | | 3677 |
| aga cgc ttc tac cag ctc acc aag ctc ctg gac tcc gtg cag cct att<br>Arg Arg Phe Tyr Gln Leu Thr Lys Leu Leu Asp Ser Val Gln Pro Ile<br>855                        860                    865                    870 | | 3725 |
| gcg aga gag ctg cat cag ttc act ttt gac ctg cta atc aag tca cac<br>Ala Arg Glu Leu His Gln Phe Thr Phe Asp Leu Leu Ile Lys Ser His<br>                875                    880                    885 | | 3773 |
| atg gtg agc gtg gac ttt ccg gaa atg atg gca gag atc atc tct gtg<br>Met Val Ser Val Asp Phe Pro Glu Met Met Ala Glu Ile Ile Ser Val<br>                    890                    895                    900 | | 3821 |
| caa gtg ccc aag atc ctt tct ggg aaa gtc aag ccc atc tat ttc cac<br>Gln Val Pro Lys Ile Leu Ser Gly Lys Val Lys Pro Ile Tyr Phe His<br>905                          910                    915 | | 3869 |
| acc cag tga agcattggaa accctatttc cccaccccag ctcatgcccc<br>Thr Gln<br>    920 | | 3918 |
| ctttcagatg tcttctgcct gttataactc tgcactactc ctctgcagtg ccttgggaa | | 3978 |
| tttcctctat tgatgtacag tctgtcatga acatgttcct gaattctatt tgctgggctt | | 4038 |
| ttttttttctc tttctctcct ttcttttttct tcttccctcc ctatctaacc ctcccatggc | | 4098 |
| accttcagac tttgcttccc attgtggctc ctatctgtgt tttgaatggt gttgtatgcc | | 4158 |
| tttaaatctg tgatgatcct catatggccc agtgtcaagt tgtgcttgtt tacagcacta | | 4218 |
| ctctgtgcca gccacacaaa cgtttactta tcttatgcca cgggaagttt agagagctaa | | 4278 |
| gattatctgg ggaaatcaaa acaaaaacaa gcaaac | | 4314 |

<210> SEQ ID NO 2
<211> LENGTH: 920
<212> TYPE: PRT
<213> ORGANISM: Homo sapiens

<400> SEQUENCE: 2

Met Glu Val Gln Leu Gly Leu Gly Arg Val Tyr Pro Arg Pro Pro Ser
1                5                      10                    15

Lys Thr Tyr Arg Gly Ala Phe Gln Asn Leu Phe Gln Ser Val Arg Glu
                20                    25                    30

Val Ile Gln Asn Pro Gly Pro Arg His Pro Glu Ala Ala Ser Ala Ala
                      35                    40                    45

```
Pro Pro Gly Ala Ser Leu Leu Leu Gln Gln Gln Gln Gln Gln
    50              55                  60
Gln Gln Gln Gln Gln Gln Gln Gln Gln Gln Gln Gln Gln Gln Gln Gln
65                  70                  75                  80
Glu Thr Ser Pro Arg Gln Gln Gln Gln Gln Gly Glu Asp Gly Ser
                85                  90                  95
Pro Gln Ala His Arg Arg Gly Pro Thr Gly Tyr Leu Val Leu Asp Glu
                100                 105                 110
Glu Gln Gln Pro Ser Gln Pro Gln Ser Ala Leu Glu Cys His Pro Glu
                115                 120                 125
Arg Gly Cys Val Pro Glu Pro Gly Ala Ala Val Ala Ala Ser Lys Gly
    130                 135                 140
Leu Pro Gln Gln Leu Pro Ala Pro Pro Asp Glu Asp Asp Ser Ala Ala
145                 150                 155                 160
Pro Ser Thr Leu Ser Leu Leu Gly Pro Thr Phe Pro Gly Leu Ser Ser
                165                 170                 175
Cys Ser Ala Asp Leu Lys Asp Ile Leu Ser Glu Ala Ser Thr Met Gln
                180                 185                 190
Leu Leu Gln Gln Gln Gln Gln Glu Ala Val Ser Glu Gly Ser Ser Ser
        195                 200                 205
Gly Arg Ala Arg Glu Ala Ser Gly Ala Pro Thr Ser Ser Lys Asp Asn
    210                 215                 220
Tyr Leu Gly Gly Thr Ser Thr Ile Ser Asp Asn Ala Lys Glu Leu Cys
225                 230                 235                 240
Lys Ala Val Ser Val Ser Met Gly Leu Gly Val Glu Ala Leu Glu His
                245                 250                 255
Leu Ser Pro Gly Glu Gln Leu Arg Gly Asp Cys Met Tyr Ala Pro Leu
                260                 265                 270
Leu Gly Val Pro Pro Ala Val Arg Pro Thr Pro Cys Ala Pro Leu Ala
        275                 280                 285
Glu Cys Lys Gly Ser Leu Leu Asp Asp Ser Ala Gly Lys Ser Thr Glu
    290                 295                 300
Asp Thr Ala Glu Tyr Ser Pro Phe Lys Gly Gly Tyr Thr Lys Gly Leu
305                 310                 315                 320
Glu Gly Glu Ser Leu Gly Cys Ser Gly Ser Ala Ala Ala Gly Ser Ser
                325                 330                 335
Gly Thr Leu Glu Leu Pro Ser Thr Leu Ser Leu Tyr Lys Ser Gly Ala
                340                 345                 350
Leu Asp Glu Ala Ala Ala Tyr Gln Ser Arg Asp Tyr Tyr Asn Phe Pro
        355                 360                 365
Leu Ala Leu Ala Gly Pro Pro Pro Pro Pro Pro Pro His Pro His
370                 375                 380
Ala Arg Ile Lys Leu Glu Asn Pro Leu Asp Tyr Gly Ser Ala Trp Ala
385                 390                 395                 400
Ala Ala Ala Ala Gln Cys Arg Tyr Gly Asp Leu Ala Ser Leu His Gly
                405                 410                 415
Ala Gly Ala Ala Gly Pro Gly Ser Gly Ser Pro Ser Ala Ala Ala Ser
        420                 425                 430
Ser Ser Trp His Thr Leu Phe Thr Ala Glu Gly Gln Leu Tyr Gly
            435                 440                 445
Pro Cys Gly Gly Gly Gly Gly Gly Gly Gly Gly Gly Gly
    450                 455                 460
Gly Gly Gly Gly Gly Gly Gly Gly Gly Glu Ala Gly Ala Val Ala Pro
```

```
              465                 470                 475                 480
            Tyr Gly Tyr Thr Arg Pro Pro Gln Gly Leu Ala Gly Gln Glu Ser Asp
                            485                 490                 495
            Phe Thr Ala Pro Asp Val Trp Tyr Pro Gly Met Val Ser Arg Val
                        500                 505                 510
            Pro Tyr Pro Ser Pro Thr Cys Val Lys Ser Glu Met Gly Pro Trp Met
                            515                 520                 525
            Asp Ser Tyr Ser Gly Pro Tyr Gly Asp Met Arg Leu Glu Thr Ala Arg
            530                 535                 540
            Asp His Val Leu Pro Ile Asp Tyr Tyr Phe Pro Pro Gln Lys Thr Cys
            545                 550                 555                 560
            Leu Ile Cys Gly Asp Glu Ala Ser Gly Cys His Tyr Gly Ala Leu Thr
                            565                 570                 575
            Cys Gly Ser Cys Lys Val Phe Phe Lys Arg Ala Ala Glu Gly Lys Gln
                        580                 585                 590
            Lys Tyr Leu Cys Ala Ser Arg Asn Asp Cys Thr Ile Asp Lys Phe Arg
                    595                 600                 605
            Arg Lys Asn Cys Pro Ser Cys Arg Leu Arg Lys Cys Tyr Glu Ala Gly
                610                 615                 620
            Met Thr Leu Gly Ala Arg Lys Leu Lys Lys Leu Gly Asn Leu Lys Leu
            625                 630                 635                 640
            Gln Glu Glu Gly Glu Ala Ser Ser Thr Thr Ser Pro Thr Glu Glu Thr
                            645                 650                 655
            Thr Gln Lys Leu Thr Val Ser His Ile Glu Gly Tyr Glu Cys Gln Pro
                        660                 665                 670
            Ile Phe Leu Asn Val Leu Glu Ala Ile Glu Pro Gly Val Val Cys Ala
                    675                 680                 685
            Gly His Asp Asn Asn Gln Pro Asp Ser Phe Ala Ala Leu Leu Ser Ser
                690                 695                 700
            Leu Asn Glu Leu Gly Glu Arg Gln Leu Val His Val Val Lys Trp Ala
            705                 710                 715                 720
            Lys Ala Leu Pro Gly Phe Arg Asn Leu His Val Asp Asp Gln Met Ala
                            725                 730                 735
            Val Ile Gln Tyr Ser Trp Met Gly Leu Met Val Phe Ala Met Gly Trp
                        740                 745                 750
            Arg Ser Phe Thr Asn Val Asn Ser Arg Met Leu Tyr Phe Ala Pro Asp
                    755                 760                 765
            Leu Val Phe Asn Glu Tyr Arg Met His Lys Ser Arg Met Tyr Ser Gln
                770                 775                 780
            Cys Val Arg Met Arg His Leu Ser Gln Glu Phe Gly Trp Leu Gln Ile
            785                 790                 795                 800
            Thr Pro Gln Glu Phe Leu Cys Met Lys Ala Leu Leu Leu Phe Ser Ile
                            805                 810                 815
            Ile Pro Val Asp Gly Leu Lys Asn Gln Lys Phe Phe Asp Glu Leu Arg
                        820                 825                 830
            Met Asn Tyr Ile Lys Glu Leu Asp Arg Ile Ile Ala Cys Lys Arg Lys
                    835                 840                 845
            Asn Pro Thr Ser Cys Ser Arg Arg Phe Tyr Gln Leu Thr Lys Leu Leu
                850                 855                 860
            Asp Ser Val Gln Pro Ile Ala Arg Glu Leu His Gln Phe Thr Phe Asp
            865                 870                 875                 880
            Leu Leu Ile Lys Ser His Met Val Ser Val Asp Phe Pro Glu Met Met
                            885                 890                 895
```

```
Ala Glu Ile Ile Ser Val Gln Val Pro Lys Ile Leu Ser Gly Lys Val
            900                 905                 910

Lys Pro Ile Tyr Phe His Thr Gln
            915                 920

<210> SEQ ID NO 3
<211> LENGTH: 2998
<212> TYPE: DNA
<213> ORGANISM: Mus musculus
<220> FEATURE:
<221> NAME/KEY: CDS
<222> LOCATION: (33)..(2732)

<400> SEQUENCE: 3
```

| | | | | | | | | | | | |
|---|---|---|---|---|---|---|---|---|---|---|---|
| gaattcggtg gaagctacag acaagctcaa gg atg gag gtg cag tta ggg ctg | | | | | | | | | | | 53 |
| | | | | Met Glu Val Gln Leu Gly Leu | | | | | | |
| | | | | 1 | | 5 | | | | | |
| gga agg gtc tac cca cgg ccc cca tcc aag acc tat cga gga gcg ttc | | | | | | | | | | | 101 |
| Gly Arg Val Tyr Pro Arg Pro Pro Ser Lys Thr Tyr Arg Gly Ala Phe | | | | | | | | | | | |
| | | 10 | | | | 15 | | | | 20 | |
| cag aat ctg ttc cag agc gtg cgc gaa gcg atc cag aac ccg ggc ccc | | | | | | | | | | | 149 |
| Gln Asn Leu Phe Gln Ser Val Arg Glu Ala Ile Gln Asn Pro Gly Pro | | | | | | | | | | | |
| | 25 | | | | 30 | | | | 35 | | |
| agg cac cct gag gcc gct aac ata gca cct ccc ggc gcc tgt tta cag | | | | | | | | | | | 197 |
| Arg His Pro Glu Ala Ala Asn Ile Ala Pro Pro Gly Ala Cys Leu Gln | | | | | | | | | | | |
| 40 | | | | 45 | | | | 50 | | | 55 |
| cag agg cag gag act agc ccc cgg cgg cgg cgg cag cag cac act | | | | | | | | | | | 245 |
| Gln Arg Gln Glu Thr Ser Pro Arg Arg Arg Arg Gln Gln His Thr | | | | | | | | | | | |
| | | | 60 | | | | 65 | | | | 70 |
| gag gat ggt tct cct caa gcc cac atc aga ggc ccc aca ggc tac ctg | | | | | | | | | | | 293 |
| Glu Asp Gly Ser Pro Gln Ala His Ile Arg Gly Pro Thr Gly Tyr Leu | | | | | | | | | | | |
| | | 75 | | | | 80 | | | | 85 | |
| gcc ctg gag gag gaa cag cag cct tca cag cag cag gca gcc tcc gag | | | | | | | | | | | 341 |
| Ala Leu Glu Glu Glu Gln Gln Pro Ser Gln Gln Gln Ala Ala Ser Glu | | | | | | | | | | | |
| | 90 | | | | 95 | | | | 100 | | |
| ggc cac cct gag agc agc tgc ctc ccc gag cct ggg gcg gcc acc gct | | | | | | | | | | | 389 |
| Gly His Pro Glu Ser Ser Cys Leu Pro Glu Pro Gly Ala Ala Thr Ala | | | | | | | | | | | |
| | 105 | | | | 110 | | | | 115 | | |
| cct ggc aag ggg ctg ccg cag cag cca cca gct cct cca gat cag gat | | | | | | | | | | | 437 |
| Pro Gly Lys Gly Leu Pro Gln Gln Pro Pro Ala Pro Pro Asp Gln Asp | | | | | | | | | | | |
| 120 | | | | 125 | | | | 130 | | | 135 |
| gac tca gct gcc cca tcc acg ttg tcc ctg ctg ggc ccc act ttc cca | | | | | | | | | | | 485 |
| Asp Ser Ala Ala Pro Ser Thr Leu Ser Leu Leu Gly Pro Thr Phe Pro | | | | | | | | | | | |
| | | | | 140 | | | | 145 | | | 150 |
| ggc tta agc agc tgc tcc gcc gac att aaa gac att ttg aac gag gcc | | | | | | | | | | | 533 |
| Gly Leu Ser Ser Cys Ser Ala Asp Ile Lys Asp Ile Leu Asn Glu Ala | | | | | | | | | | | |
| | | 155 | | | | 160 | | | | 165 | |
| ggc acc atg caa ctt ctt cag cag cag caa cag cag cag cac caa | | | | | | | | | | | 581 |
| Gly Thr Met Gln Leu Leu Gln Gln Gln Gln Gln Gln Gln His Gln | | | | | | | | | | | |
| | | | 170 | | | | 175 | | | | 180 |
| cag cag cac caa cag cac caa cag cag cag gag gta atc tcc gaa ggc | | | | | | | | | | | 629 |
| Gln Gln His Gln Gln His Gln Gln Gln Glu Val Ile Ser Glu Gly | | | | | | | | | | | |
| | | 185 | | | | 190 | | | | 195 | |
| agc agc gca aga gcc agg gag gcc acg ggg gct ccc tct tcc tcc aag | | | | | | | | | | | 677 |
| Ser Ser Ala Arg Ala Arg Glu Ala Thr Gly Ala Pro Ser Ser Ser Lys | | | | | | | | | | | |
| 200 | | | | 205 | | | | 210 | | | 215 |
| gat agt tac cta ggg ggc aat tca acc ata tct gac agt gcc aag gag | | | | | | | | | | | 725 |
| Asp Ser Tyr Leu Gly Gly Asn Ser Thr Ile Ser Asp Ser Ala Lys Glu | | | | | | | | | | | |
| | | | | 220 | | | | 225 | | | 230 |
| ttg tgt aaa gca gtg tct gtg tcc atg gga ttg ggt gtg gaa gca ttg | | | | | | | | | | | 773 |

```
Leu Cys Lys Ala Val Ser Val Ser Met Gly Leu Gly Val Glu Ala Leu
            235                 240                 245 gaa cat ctg agt cca ggg gaa cag ctt cgg gga gac tgc atg tac gcg      821
Glu His Leu Ser Pro Gly Glu Gln Leu Arg Gly Asp Cys Met Tyr Ala
            250                 255                 260 tcg ctc ctg gga ggt cca ccc gcg gtg cgt ccc act cct tgt gcg ccg      869
Ser Leu Leu Gly Gly Pro Pro Ala Val Arg Pro Thr Pro Cys Ala Pro
            265                 270                 275 ctg ccc gaa tgc aaa ggt ctt ccc ctg gac gaa ggc cca ggc aaa agc      917
Leu Pro Glu Cys Lys Gly Leu Pro Leu Asp Glu Gly Pro Gly Lys Ser
280                 285                 290                 295 act gaa gag act gct gag tat tcc tct ttc aag gga ggt tac gcc aaa      965
Thr Glu Glu Thr Ala Glu Tyr Ser Ser Phe Lys Gly Gly Tyr Ala Lys
                300                 305                 310 gga ttg gaa ggt gag agc ttg ggg tgc tct ggc agc agt gaa gca ggt     1013
Gly Leu Glu Gly Glu Ser Leu Gly Cys Ser Gly Ser Ser Glu Ala Gly
            315                 320                 325 agc tct ggg aca ctt gag atc ccg tcc tct ctg tct ctg tat aaa tct     1061
Ser Ser Gly Thr Leu Glu Ile Pro Ser Ser Leu Ser Leu Tyr Lys Ser
            330                 335                 340 gga gca cta gac gag gca gca gca tac cag aat cgc gac tac tac aac     1109
Gly Ala Leu Asp Glu Ala Ala Ala Tyr Gln Asn Arg Asp Tyr Tyr Asn
345                 350                 355 ttt ccg ctg gct ctg tcc ggg ccg ccg cac ccc ccg ccc cct acc cat     1157
Phe Pro Leu Ala Leu Ser Gly Pro Pro His Pro Pro Pro Pro Thr His
360                 365                 370                 375 cca cac gcc cgt atc aag ctg gag aac cca ttg gac tac ggc agc gcc     1205
Pro His Ala Arg Ile Lys Leu Glu Asn Pro Leu Asp Tyr Gly Ser Ala
                380                 385                 390 tgg gct gcg gcg gca gcg caa tgc cgc tat ggg gac ttg ggt agt cta     1253
Trp Ala Ala Ala Ala Ala Gln Cys Arg Tyr Gly Asp Leu Gly Ser Leu
            395                 400                 405 cat gga ggg agt gta gcc ggg ccc agc act gga tcg ccc cca gcc acc     1301
His Gly Gly Ser Val Ala Gly Pro Ser Thr Gly Ser Pro Pro Ala Thr
            410                 415                 420 acc tct tct tcc tgg cat act ctc ttc aca gct gaa gaa ggc caa tta     1349
Thr Ser Ser Ser Trp His Thr Leu Phe Thr Ala Glu Glu Gly Gln Leu
            425                 430                 435 tat ggg cca gga ggc ggg ggc ggc agc agc agc cca agc gat gcc ggg     1397
Tyr Gly Pro Gly Gly Gly Gly Gly Ser Ser Ser Pro Ser Asp Ala Gly
440                 445                 450                 455 cct gta gcc ccc tat ggc tac act cgg ccc cct cag ggg ctg aca agc     1445
Pro Val Ala Pro Tyr Gly Tyr Thr Arg Pro Pro Gln Gly Leu Thr Ser
                460                 465                 470 cag gag agt gac tac tct gcc tcc gaa gtg tgg tat cct ggt gga gtt     1493
Gln Glu Ser Asp Tyr Ser Ala Ser Glu Val Trp Tyr Pro Gly Gly Val
            475                 480                 485 gtg aac aga gta ccc tat ccc agt ccc aat tgt gtc aaa agt gaa atg     1541
Val Asn Arg Val Pro Tyr Pro Ser Pro Asn Cys Val Lys Ser Glu Met
            490                 495                 500 gga cct tgg atg gag aac tac tcc gga cct tat ggg gac atg cgt ttg     1589
Gly Pro Trp Met Glu Asn Tyr Ser Gly Pro Tyr Gly Asp Met Arg Leu
            505                 510                 515 gac agt acc agg gac cat gtt tta ccc atc gac tat tac ttt cca ccc     1637
Asp Ser Thr Arg Asp His Val Leu Pro Ile Asp Tyr Tyr Phe Pro Pro
520                 525                 530                 535 cag aag acc tgc ctg atc tgt gga gat gaa gct tct ggc tgt cac tac     1685
Gln Lys Thr Cys Leu Ile Cys Gly Asp Glu Ala Ser Gly Cys His Tyr
                540                 545                 550
```

| | | |
|---|---|---|
| gga gct ctc act tgt ggc agc tgc aag gtc ttc ttc aaa aga gcc gct<br>Gly Ala Leu Thr Cys Gly Ser Cys Lys Val Phe Phe Lys Arg Ala Ala<br>555 560 565 | | 1733 |
| gaa ggg aaa cag aag tat cta tgt gcc agc aga aac gat tgt acc att<br>Glu Gly Lys Gln Lys Tyr Leu Cys Ala Ser Arg Asn Asp Cys Thr Ile<br>570 575 580 | | 1781 |
| gat aaa ttt cgg agg aaa aat tgc cca tct tgt cgt ctc cgg aaa tgt<br>Asp Lys Phe Arg Arg Lys Asn Cys Pro Ser Cys Arg Leu Arg Lys Cys<br>585 590 595 | | 1829 |
| tat gaa gca ggg atg act ctg gga gct cgt aag ctg aag aaa ctt gga<br>Tyr Glu Ala Gly Met Thr Leu Gly Ala Arg Lys Leu Lys Lys Leu Gly<br>600 605 610 615 | | 1877 |
| aat cta aaa cta cag gag gaa gga gaa aac tcc aat gct ggc agc ccc<br>Asn Leu Lys Leu Gln Glu Glu Gly Glu Asn Ser Asn Ala Gly Ser Pro<br>620 625 630 | | 1925 |
| act gag gac cca tcc cag aag atg act gta tca cac att gaa ggc tat<br>Thr Glu Asp Pro Ser Gln Lys Met Thr Val Ser His Ile Glu Gly Tyr<br>635 640 645 | | 1973 |
| gaa tgt cag cct atc ttt ctt aac gtc ctg gaa gcc att gag cca gga<br>Glu Cys Gln Pro Ile Phe Leu Asn Val Leu Glu Ala Ile Glu Pro Gly<br>650 655 660 | | 2021 |
| gtg gtg tgt gcc gga cat gac aac aac caa cca gat tcc ttt gct gcc<br>Val Val Cys Ala Gly His Asp Asn Asn Gln Pro Asp Ser Phe Ala Ala<br>665 670 675 | | 2069 |
| ttg tta tct agc ctc aat gag ctt gga gag agg cag ctt gtg cat gtg<br>Leu Leu Ser Ser Leu Asn Glu Leu Gly Glu Arg Gln Leu Val His Val<br>680 685 690 695 | | 2117 |
| gtc aag tgg gcc aag gcc ttg cct ggc ttc cgc aac ttg cat gtg gat<br>Val Lys Trp Ala Lys Ala Leu Pro Gly Phe Arg Asn Leu His Val Asp<br>700 705 710 | | 2165 |
| gac cag atg gcg gtc att cag tat tcc tgg atg gga ctg atg gta ttt<br>Asp Gln Met Ala Val Ile Gln Tyr Ser Trp Met Gly Leu Met Val Phe<br>715 720 725 | | 2213 |
| gcc atg ggt tgg cgg tcc ttc act aat gtc aac tcc agg atg ctc tac<br>Ala Met Gly Trp Arg Ser Phe Thr Asn Val Asn Ser Arg Met Leu Tyr<br>730 735 740 | | 2261 |
| ttt gca cct gac ttg gtt ttc aat gag tac cgc atg cac aag tct cgg<br>Phe Ala Pro Asp Leu Val Phe Asn Glu Tyr Arg Met His Lys Ser Arg<br>745 750 755 | | 2309 |
| atg tac agc cag tgt gtg agg atg agg cac ctg tct caa gag ttt gga<br>Met Tyr Ser Gln Cys Val Arg Met Arg His Leu Ser Gln Glu Phe Gly<br>760 765 770 775 | | 2357 |
| tgg ctc caa ata acc ccc cag gaa ttc ctg tgc atg aaa gca ctg ctg<br>Trp Leu Gln Ile Thr Pro Gln Glu Phe Leu Cys Met Lys Ala Leu Leu<br>780 785 790 | | 2405 |
| ctc ttc agc att att cca gtg gat ggg ctg aaa aat caa aaa ttc ttt<br>Leu Phe Ser Ile Ile Pro Val Asp Gly Leu Lys Asn Gln Lys Phe Phe<br>795 800 805 | | 2453 |
| gat gaa ctt cga atg aac tac atc aag gaa ctc gat cgc atc att gca<br>Asp Glu Leu Arg Met Asn Tyr Ile Lys Glu Leu Asp Arg Ile Ile Ala<br>810 815 820 | | 2501 |
| tgc aaa aga aag aat ccc aca tcc tgc tca agg cgc ttc tac cag ctc<br>Cys Lys Arg Lys Asn Pro Thr Ser Cys Ser Arg Arg Phe Tyr Gln Leu<br>825 830 835 | | 2549 |
| acc aag ctc ctg gat tct gtg cag cct att gca aga gag ctg cat cag<br>Thr Lys Leu Leu Asp Ser Val Gln Pro Ile Ala Arg Glu Leu His Gln<br>840 845 850 855 | | 2597 |
| ttc act ttt gac ctg cta atc aag tcc cat atg gtg agc gtg gac ttt<br>Phe Thr Phe Asp Leu Leu Ile Lys Ser His Met Val Ser Val Asp Phe<br>860 865 870 | | 2645 |

-continued

```
cct gaa atg atg gca gag atc atc tct gtg caa gtg ccc aag atc ctt      2693
Pro Glu Met Met Ala Glu Ile Ile Ser Val Gln Val Pro Lys Ile Leu
            875                 880                 885 tct ggg aaa gtc aag ccc atc tat ttc cac aca cag tga agatttggaa       2742
Ser Gly Lys Val Lys Pro Ile Tyr Phe His Thr Gln
        890                 895 accctaatac ccaaaaccca ccttgttccc tttccagatg tcttctgcct gttatataac    2802
tctgcactac ttctctgcag tgccttgggg gaaattcctc tactgatgta cagtctgtcg    2862
tgaacaggtt cctcagttct atttcctggg cttctccttc ttttttttc ttcttccctc     2922 cctctttcac cctcccatgg cacattttga atctgctgct gattgtggct ctgcctttgt    2982
tttgatttct gttgta                                                    2998
```

<210> SEQ ID NO 4
<211> LENGTH: 899
<212> TYPE: PRT
<213> ORGANISM: Mus musculus

<400> SEQUENCE: 4

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Asn Ile Ala
        35                  40                  45

Pro Pro Gly Ala Cys Leu Gln Gln Arg Gln Glu Thr Ser Pro Arg Arg
    50                  55                  60

Arg Arg Arg Gln Gln His Thr Glu Asp Gly Ser Pro Gln Ala His Ile
65                  70                  75                  80

Arg Gly Pro Thr Gly Tyr Leu Ala Leu Glu Glu Gln Gln Pro Ser
                85                  90                  95

Gln Gln Gln Ala Ala Ser Glu Gly His Pro Glu Ser Ser Cys Leu Pro
            100                 105                 110

Glu Pro Gly Ala Ala Thr Ala Pro Gly Lys Gly Leu Pro Gln Gln Pro
        115                 120                 125

Pro Ala Pro Pro Asp Gln Asp Asp Ser Ala Ala Pro Ser Thr Leu Ser
    130                 135                 140

Leu Leu Gly Pro Thr Phe Pro Gly Leu Ser Ser Cys Ser Ala Asp Ile
145                 150                 155                 160

Lys Asp Ile Leu Asn Glu Ala Gly Thr Met Gln Leu Leu Gln Gln Gln
                165                 170                 175

Gln Gln Gln Gln His Gln Gln His Gln Gln His Gln Gln Gln
            180                 185                 190

Gln Glu Val Ile Ser Glu Gly Ser Ser Ala Arg Ala Arg Glu Ala Thr
        195                 200                 205

Gly Ala Pro Ser Ser Ser Lys Asp Ser Tyr Leu Gly Gly Asn Ser Thr
    210                 215                 220

Ile Ser Asp Ser Ala Lys Glu Leu Cys Lys Ala Val Ser Val Ser Met
225                 230                 235                 240

Gly Leu Gly Val Glu Ala Leu Glu His Leu Ser Pro Gly Glu Gln Leu
                245                 250                 255

Arg Gly Asp Cys Met Tyr Ala Ser Leu Leu Gly Gly Pro Pro Ala Val
            260                 265                 270

Arg Pro Thr Pro Cys Ala Pro Leu Pro Glu Cys Lys Gly Leu Pro Leu
```

```
                275                 280                 285
Asp Glu Gly Pro Gly Lys Ser Thr Glu Thr Ala Glu Tyr Ser Ser
290                 295                 300

Phe Lys Gly Gly Tyr Ala Lys Gly Leu Glu Gly Ser Leu Gly Cys
305                 310                 315                 320

Ser Gly Ser Ser Glu Ala Gly Ser Ser Gly Thr Leu Glu Ile Pro Ser
                325                 330                 335

Ser Leu Ser Leu Tyr Lys Ser Gly Ala Leu Asp Glu Ala Ala Tyr
            340                 345                 350

Gln Asn Arg Asp Tyr Tyr Asn Phe Pro Leu Ala Leu Ser Gly Pro Pro
                355                 360                 365

His Pro Pro Pro Thr His Pro His Ala Arg Ile Lys Leu Glu Asn
        370                 375                 380

Pro Leu Asp Tyr Gly Ser Ala Trp Ala Ala Ala Ala Gln Cys Arg
385                 390                 395                 400

Tyr Gly Asp Leu Gly Ser Leu His Gly Gly Ser Val Ala Gly Pro Ser
                405                 410                 415

Thr Gly Ser Pro Pro Ala Thr Thr Ser Ser Ser Trp His Thr Leu Phe
                420                 425                 430

Thr Ala Glu Glu Gly Gln Leu Tyr Gly Pro Gly Gly Gly Gly Ser
        435                 440                 445

Ser Ser Pro Ser Asp Ala Gly Pro Val Ala Pro Tyr Gly Tyr Thr Arg
450                 455                 460

Pro Pro Gln Gly Leu Thr Ser Gln Glu Ser Asp Tyr Ser Ala Ser Glu
465                 470                 475                 480

Val Trp Tyr Pro Gly Gly Val Val Asn Arg Val Pro Tyr Pro Ser Pro
                485                 490                 495

Asn Cys Val Lys Ser Glu Met Gly Pro Trp Met Glu Asn Tyr Ser Gly
                500                 505                 510

Pro Tyr Gly Asp Met Arg Leu Asp Ser Thr Arg Asp His Val Leu Pro
        515                 520                 525

Ile Asp Tyr Tyr Phe Pro Pro Gln Lys Thr Cys Leu Ile Cys Gly Asp
530                 535                 540

Glu Ala Ser Gly Cys His Tyr Gly Ala Leu Thr Cys Gly Ser Cys Lys
545                 550                 555                 560

Val Phe Phe Lys Arg Ala Ala Glu Gly Lys Gln Lys Tyr Leu Cys Ala
                565                 570                 575

Ser Arg Asn Asp Cys Thr Ile Asp Lys Phe Arg Arg Lys Asn Cys Pro
            580                 585                 590

Ser Cys Arg Leu Arg Lys Cys Tyr Glu Ala Gly Met Thr Leu Gly Ala
        595                 600                 605

Arg Lys Leu Lys Lys Leu Gly Asn Leu Lys Leu Gln Glu Glu Gly Glu
    610                 615                 620

Asn Ser Asn Ala Gly Ser Pro Thr Glu Asp Pro Ser Gln Lys Met Thr
625                 630                 635                 640

Val Ser His Ile Glu Gly Tyr Glu Cys Gln Pro Ile Phe Leu Asn Val
                645                 650                 655

Leu Glu Ala Ile Glu Pro Gly Val Val Cys Ala Gly His Asp Asn Asn
                660                 665                 670

Gln Pro Asp Ser Phe Ala Ala Leu Leu Ser Ser Leu Asn Glu Leu Gly
            675                 680                 685

Glu Arg Gln Leu Val His Val Val Lys Trp Ala Lys Ala Leu Pro Gly
        690                 695                 700
```

```
Phe Arg Asn Leu His Val Asp Asp Gln Met Ala Val Ile Gln Tyr Ser
705                 710                 715                 720

Trp Met Gly Leu Met Val Phe Ala Met Gly Trp Arg Ser Phe Thr Asn
            725                 730                 735

Val Asn Ser Arg Met Leu Tyr Phe Ala Pro Asp Leu Val Phe Asn Glu
        740                 745                 750

Tyr Arg Met His Lys Ser Arg Met Tyr Ser Gln Cys Val Arg Met Arg
    755                 760                 765

His Leu Ser Gln Glu Phe Gly Trp Leu Gln Ile Thr Pro Gln Glu Phe
770                 775                 780

Leu Cys Met Lys Ala Leu Leu Leu Phe Ser Ile Ile Pro Val Asp Gly
785                 790                 795                 800

Leu Lys Asn Gln Lys Phe Phe Asp Glu Leu Arg Met Asn Tyr Ile Lys
                805                 810                 815

Glu Leu Asp Arg Ile Ile Ala Cys Lys Arg Lys Asn Pro Thr Ser Cys
            820                 825                 830

Ser Arg Arg Phe Tyr Gln Leu Thr Lys Leu Leu Asp Ser Val Gln Pro
        835                 840                 845

Ile Ala Arg Glu Leu His Gln Phe Thr Phe Asp Leu Leu Ile Lys Ser
    850                 855                 860

His Met Val Ser Val Asp Phe Pro Glu Met Met Ala Glu Ile Ile Ser
865                 870                 875                 880

Val Gln Val Pro Lys Ile Leu Ser Gly Lys Val Lys Pro Ile Tyr Phe
                885                 890                 895

His Thr Gln

<210> SEQ ID NO 5
<211> LENGTH: 4137
<212> TYPE: DNA
<213> ORGANISM: Rattus norvegicus
<220> FEATURE:
<221> NAME/KEY: CDS
<222> LOCATION: (994)..(3702)

<400> SEQUENCE: 5
atccctagga gccagcctgc tgggagaacc agagggtccg gagcaaacct ggaggctgag      60
agggcatcag aggggaaaag actgagttag ccactccagt gccatacaga agcttaaggg     120
acataccacg ccagccccag cccagcgaca gccaacgcct gttgcagagc ggcggcttcg     180
aagccgccgc ccagaagctg ccctttcctc ttcggtgaag tttctaaaag ctgcgggaga     240
ctcggaggaa gcgaagaaag tgtccggtag gactacgact gcctttgtcc tcctccctcc     300
taccctacc  cctcctgggt cccctctccc tgagcggact aggcaggctt cctggccagc     360
cctctcccct acaccaccag ctctgccagc cagtttgcac agaggtaact cccttttggct    420
gaaagcagac gagcttgttg cccattggaa gggaggcttt tgggagccca gagactgagg     480
agcaacagca cgctggagag tccctgattc caggttctcc cccctgcacc tcctactgcc     540
cgcccctcac cctgtgtgtg cagctagaat tgaaagatg aaaagacagt tggggcttca     600
gtagtcgaaa gcaaacaaa agcaaaaaga aacaaaaag aaaatagccc agttcttatt      660
tgcacctgct tcagtggaca ttgactttgg aaggcagaga attttccttc cccccagtca     720
agctttgagc atctttaat  ctgttcttca agtatttagg gacaaactgt gaaactagca     780
gggcagatcc tgtctagcgc gtgccttcct ttacaggaga ctttgaggct atctgggcgc     840
tcccccccct ccctgcaagt tttcttccct ggagcttccc gcaggtgggc agctagctgc     900
```

-continued

```
agatactaca tcatcagtca gtagaactct tcagagcaag agacgaggag gcaggataag        960
ggaattcggt ggaagctaga gacaagctaa agg atg gag gtg cag tta ggg ctg       1014
                                    Met Glu Val Gln Leu Gly Leu
                                    1               5 gga agg gtc tac cca cgg ccc ccg tcc aag acc tat cga gga gcg ttc        1062
Gly Arg Val Tyr Pro Arg Pro Pro Ser Lys Thr Tyr Arg Gly Ala Phe
        10              15                  20 cag aat ctg ttc cag agc gtg cgc gaa gcg atc cag aac ccg ggc ccc        1110
Gln Asn Leu Phe Gln Ser Val Arg Glu Ala Ile Gln Asn Pro Gly Pro
25                  30                  35 agg cac cct gag gcc gct agc ata gca cct ccc ggt gcc tgt tta cag        1158
Arg His Pro Glu Ala Ala Ser Ile Ala Pro Pro Gly Ala Cys Leu Gln
40                  45                  50                  55 cag cgg cag gag act agc ccc cgg cgg cgg cgg cag cag cac cct            1206
Gln Arg Gln Glu Thr Ser Pro Arg Arg Arg Arg Gln Gln His Pro
                60                  65                  70 gag gat ggc tct cct caa gcc cac atc aga ggc acc aca ggc tac ctg        1254
Glu Asp Gly Ser Pro Gln Ala His Ile Arg Gly Thr Thr Gly Tyr Leu
            75                  80                  85 gcc ctg gag gag gaa cag cag cct tca cag cag cag tca gcc tcc gag        1302
Ala Leu Glu Glu Glu Gln Gln Pro Ser Gln Gln Gln Ser Ala Ser Glu
        90                  95                  100 ggc cac cct gag agc ggc tgc ctc ccg gag cct gga gct gcc acg gct        1350
Gly His Pro Glu Ser Gly Cys Leu Pro Glu Pro Gly Ala Ala Thr Ala
    105                 110                 115 cct ggc aag ggg ctg ccg cag cag cca cca gct cct cca gat cag gat        1398
Pro Gly Lys Gly Leu Pro Gln Gln Pro Pro Ala Pro Pro Asp Gln Asp
120                 125                 130                 135 gac tca gct gcc cca tcc acg ttg tcc cta ctg ggc ccc act ttc cca        1446
Asp Ser Ala Ala Pro Ser Thr Leu Ser Leu Leu Gly Pro Thr Phe Pro
                140                 145                 150 ggc tta agc agc tgc tcc gca gac att aaa gac atc ctg agc gag gcc        1494
Gly Leu Ser Ser Cys Ser Ala Asp Ile Lys Asp Ile Leu Ser Glu Ala
            155                 160                 165 ggc acc atg caa ctt ctt cag cag cag cag caa cag caa cag cag cag        1542
Gly Thr Met Gln Leu Leu Gln Gln Gln Gln Gln Gln Gln Gln Gln Gln
        170                 175                 180 cag cag cag cag cag cag cag cag caa cag cag cag gag gta ata tcc        1590
Gln Gln Gln Gln Gln Gln Gln Gln Gln Gln Gln Gln Glu Val Ile Ser
    185                 190                 195 gaa ggc agc agc agc gtg aga gca agg gag gcc act ggg gct ccc tct        1638
Glu Gly Ser Ser Ser Val Arg Ala Arg Glu Ala Thr Gly Ala Pro Ser
200                 205                 210                 215 tcc tcc aag gat agt tac cta ggg ggc aat tcg acc ata tct gac agt        1686
Ser Ser Lys Asp Ser Tyr Leu Gly Gly Asn Ser Thr Ile Ser Asp Ser
                220                 225                 230 gcc aag gag ttg tgt aaa gca gtg tct gtg tcc atg ggg ttg ggt gtg        1734
Ala Lys Glu Leu Cys Lys Ala Val Ser Val Ser Met Gly Leu Gly Val
            235                 240                 245 gaa gca ctg gaa cat ctg agt cca ggg gag cag ctt cgg ggc gac tgc        1782
Glu Ala Leu Glu His Leu Ser Pro Gly Glu Gln Leu Arg Gly Asp Cys
        250                 255                 260 atg tac gcg tcg ctc ctg gga ggt cca ccc gcc gtg cgt ccc act cct        1830
Met Tyr Ala Ser Leu Leu Gly Gly Pro Pro Ala Val Arg Pro Thr Pro
    265                 270                 275 tgt gcg cct ctg gcc gaa tgc aaa ggt ctt tcc ctg gac gaa ggc ccg        1878
Cys Ala Pro Leu Ala Glu Cys Lys Gly Leu Ser Leu Asp Glu Gly Pro
280                 285                 290                 295
```

-continued

| | |
|---|---|
| ggc aaa ggc act gaa gag act gct gag tat tcc tct ttc aag gga ggt<br>Gly Lys Gly Thr Glu Glu Thr Ala Glu Tyr Ser Ser Phe Lys Gly Gly<br>300 305 310 | 1926 |
| tac gcc aaa ggg ttg gaa ggt gag agt ctg ggc tgc tct ggc agc agt<br>Tyr Ala Lys Gly Leu Glu Gly Glu Ser Leu Gly Cys Ser Gly Ser Ser<br>315 320 325 | 1974 |
| gaa gca ggt agc tct ggg aca ctt gag atc ccg tcc tca ctg tct ctg<br>Glu Ala Gly Ser Ser Gly Thr Leu Glu Ile Pro Ser Ser Leu Ser Leu<br>330 335 340 | 2022 |
| tat aag tct gga gca gta gac gag gca gca gca tac cag aat cgc gac<br>Tyr Lys Ser Gly Ala Val Asp Glu Ala Ala Ala Tyr Gln Asn Arg Asp<br>345 350 355 | 2070 |
| tac tac aac ttt ccg ctc gct ctg tcc ggg ccg ccg cac ccc ccg ccc<br>Tyr Tyr Asn Phe Pro Leu Ala Leu Ser Gly Pro Pro His Pro Pro Pro<br>360 365 370 375 | 2118 |
| cct acc cat cca cac gcc cgc atc aag ctg gag aac ccg tcg gac tac<br>Pro Thr His Pro His Ala Arg Ile Lys Leu Glu Asn Pro Ser Asp Tyr<br>380 385 390 | 2166 |
| ggc agc gcc tgg gct gcg gcg gca gcg caa tgc cgc tat ggg gac ttg<br>Gly Ser Ala Trp Ala Ala Ala Ala Gln Cys Arg Tyr Gly Asp Leu<br>395 400 405 | 2214 |
| gct agc cta cat gga ggg agt gta gcc gga ccc agc act gga tcg ccc<br>Ala Ser Leu His Gly Gly Ser Val Ala Gly Pro Ser Thr Gly Ser Pro<br>410 415 420 | 2262 |
| cca gcc acc gcc tct tct tcc tgg cat act ctc ttc aca gct gaa gaa<br>Pro Ala Thr Ala Ser Ser Ser Trp His Thr Leu Phe Thr Ala Glu Glu<br>425 430 435 | 2310 |
| ggc caa tta tat ggg cca gga ggc ggg ggc ggc agc agt agc cca agc<br>Gly Gln Leu Tyr Gly Pro Gly Gly Gly Gly Ser Ser Ser Pro Ser<br>440 445 450 455 | 2358 |
| gat gct ggg cct gta gcc ccc tat ggc tac act cgg ccc cct cag ggg<br>Asp Ala Gly Pro Val Ala Pro Tyr Gly Tyr Thr Arg Pro Pro Gln Gly<br>460 465 470 | 2406 |
| ctg gca agc cag gag ggt gac ttc tct gcc tct gaa gtg tgg tat cct<br>Leu Ala Ser Gln Glu Gly Asp Phe Ser Ala Ser Glu Val Trp Tyr Pro<br>475 480 485 | 2454 |
| ggt gga gtt gtg aac aga gtc ccc tat ccc agt ccc agt tgt gtt aaa<br>Gly Gly Val Val Asn Arg Val Pro Tyr Pro Ser Pro Ser Cys Val Lys<br>490 495 500 | 2502 |
| agt gaa atg gga cct tgg atg gag aac tac tcc gga cct tat ggg gac<br>Ser Glu Met Gly Pro Trp Met Glu Asn Tyr Ser Gly Pro Tyr Gly Asp<br>505 510 515 | 2550 |
| atg cgt ttg gac agt acc agg gac cac gtt tta ccc atc gac tat tac<br>Met Arg Leu Asp Ser Thr Arg Asp His Val Leu Pro Ile Asp Tyr Tyr<br>520 525 530 535 | 2598 |
| ttc cca ccc cag aag acc tgc ctg atc tgt gga gat gaa gct tct ggt<br>Phe Pro Pro Gln Lys Thr Cys Leu Ile Cys Gly Asp Glu Ala Ser Gly<br>540 545 550 | 2646 |
| tgt cac tac gga gct ctc act tgt ggc agc tgc aag gtc ttc ttc aaa<br>Cys His Tyr Gly Ala Leu Thr Cys Gly Ser Cys Lys Val Phe Phe Lys<br>555 560 565 | 2694 |
| aga gct gcg gaa ggg aaa cag aag tat cta tgt gcc agc aga aat gat<br>Arg Ala Ala Glu Gly Lys Gln Lys Tyr Leu Cys Ala Ser Arg Asn Asp<br>570 575 580 | 2742 |
| tgc acc att gat aaa ttt cgg agg aaa aat tgt cca tcg tgt cgt ctc<br>Cys Thr Ile Asp Lys Phe Arg Arg Lys Asn Cys Pro Ser Cys Arg Leu<br>585 590 595 | 2790 |
| cgg aaa tgt tat gaa gca ggg atg act ctg gga gct cgt aag ctg aag<br>Arg Lys Cys Tyr Glu Ala Gly Met Thr Leu Gly Ala Arg Lys Leu Lys<br>600 605 610 615 | 2838 |

```
aaa ctt gga aat ctc aaa cta cag gaa gaa gga gaa aac tcc agt gct    2886
Lys Leu Gly Asn Leu Lys Leu Gln Glu Glu Gly Glu Asn Ser Ser Ala
            620                 625                 630 ggt agc ccc act gag gac cca tcc cag aag atg act gta tca cac att    2934
Gly Ser Pro Thr Glu Asp Pro Ser Gln Lys Met Thr Val Ser His Ile
                635                 640                 645 gaa ggc tat gaa tgt caa cct atc ttt ctt aat gtc ctg gaa gcc att    2982
Glu Gly Tyr Glu Cys Gln Pro Ile Phe Leu Asn Val Leu Glu Ala Ile
                    650                 655                 660 gag cca gga gtg gtg tgt gcc gga cat gac aac aac cag cct gat tcc    3030
Glu Pro Gly Val Val Cys Ala Gly His Asp Asn Asn Gln Pro Asp Ser
                665                 670                 675 ttt gct gcc ttg tta tct agt ctc aac gag ctt ggc gag aga cag ctt    3078
Phe Ala Ala Leu Leu Ser Ser Leu Asn Glu Leu Gly Glu Arg Gln Leu
680                 685                 690                 695 gta cat gtg gtc aag tgg gcc aag gcc ttg cct ggc ttc cgc aac ttg    3126
Val His Val Val Lys Trp Ala Lys Ala Leu Pro Gly Phe Arg Asn Leu
                    700                 705                 710 cat gtg gat gac cag atg gca gtc att cag tat tcc tgg atg gga ctg    3174
His Val Asp Asp Gln Met Ala Val Ile Gln Tyr Ser Trp Met Gly Leu
                715                 720                 725 atg gta ttt gcc atg ggt tgg cgg tcc ttc act aat gtc aac tct agg    3222
Met Val Phe Ala Met Gly Trp Arg Ser Phe Thr Asn Val Asn Ser Arg
                730                 735                 740 atg ctc tac ttt gca cct gac ctg gtt ttc aat gag tat cgc atg cac    3270
Met Leu Tyr Phe Ala Pro Asp Leu Val Phe Asn Glu Tyr Arg Met His
                    745                 750                 755 aag tct cga atg tac agc cag tgc gtg agg atg agg cac ctt tct caa    3318
Lys Ser Arg Met Tyr Ser Gln Cys Val Arg Met Arg His Leu Ser Gln
760                 765                 770                 775 gag ttt gga tgg ctc cag ata acc ccc cag gaa ttc ctg tgc atg aaa    3366
Glu Phe Gly Trp Leu Gln Ile Thr Pro Gln Glu Phe Leu Cys Met Lys
                    780                 785                 790 gca ctg cta ctc ttc agc att att cca gtg gat ggg ctg aaa aat caa    3414
Ala Leu Leu Leu Phe Ser Ile Ile Pro Val Asp Gly Leu Lys Asn Gln
                795                 800                 805 aaa ttc ttt gat gaa ctt cga atg aac tac atc aag gaa ctt gat cgc    3462
Lys Phe Phe Asp Glu Leu Arg Met Asn Tyr Ile Lys Glu Leu Asp Arg
                    810                 815                 820 atc att gca tgc aaa aga aaa aat ccc aca tcc tgc tca agg cgc ttc    3510
Ile Ile Ala Cys Lys Arg Lys Asn Pro Thr Ser Cys Ser Arg Arg Phe
825                 830                 835 tac cag ctc acc aag ctc ctg gat tct gtg cag cct att gca aga gag    3558
Tyr Gln Leu Thr Lys Leu Leu Asp Ser Val Gln Pro Ile Ala Arg Glu
840                 845                 850                 855 ctg cat caa ttc act ttt gac ctg cta atc aag tcc cat atg gtg agc    3606
Leu His Gln Phe Thr Phe Asp Leu Leu Ile Lys Ser His Met Val Ser
                860                 865                 870 gtg gac ttt cct gaa atg atg gca gag atc atc tct gtg caa gtg ccc    3654
Val Asp Phe Pro Glu Met Met Ala Glu Ile Ile Ser Val Gln Val Pro
                    875                 880                 885 aag atc ctt tct ggg aaa gtc aag ccc atc tat ttc cac aca cag tga    3702
Lys Ile Leu Ser Gly Lys Val Lys Pro Ile Tyr Phe His Thr Gln
                890                 895                 900 agatttggaa accctaatac ccaaacccac cttgttccct tttcagatgt cttctgcctg    3762
ttatataact ctgcactact tctctggcat gggccttggg ggaaattcct ctactgatgt    3822
acagtctgtc atgaacatgt tccccaagtt ctatttcctg ggcttttcct tctttctttt    3882
```

```
tcttcttctc tgcctctttt accctcccat ggcacatttt gaatccgctg cgtgttgtgg   3942
ctcctgcctg tgttttgagt tttgttgtat ttcttcaagt ctgtgatgat cttcttgtgg   4002
cccagtgtca actgtgcttg tttatagcac tgtgctgtgt gccaaccaag caaatgttta   4062
ctcaccttat gccatggcaa gtttagagag ctataagtat cttgggaaga aacaaacaga   4122
gagagtaaaa aaacc                                                    4137
```

<210> SEQ ID NO 6
<211> LENGTH: 902
<212> TYPE: PRT
<213> ORGANISM: Rattus norvegicus

<400> SEQUENCE: 6

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Ser Ile Ala
        35                  40                  45

Pro Pro Gly Ala Cys Leu Gln Gln Arg Gln Glu Thr Ser Pro Arg Arg
    50                  55                  60

Arg Arg Arg Gln Gln His Pro Glu Asp Gly Ser Pro Gln Ala His Ile
65                  70                  75                  80

Arg Gly Thr Thr Gly Tyr Leu Ala Leu Glu Glu Gln Gln Pro Ser
                85                  90                  95

Gln Gln Gln Ser Ala Ser Glu Gly His Pro Glu Ser Gly Cys Leu Pro
            100                 105                 110

Glu Pro Gly Ala Ala Thr Ala Pro Gly Lys Gly Leu Pro Gln Gln Pro
        115                 120                 125

Pro Ala Pro Pro Asp Gln Asp Asp Ser Ala Ala Pro Ser Thr Leu Ser
    130                 135                 140

Leu Leu Gly Pro Thr Phe Pro Gly Leu Ser Ser Cys Ser Ala Asp Ile
145                 150                 155                 160

Lys Asp Ile Leu Ser Glu Ala Gly Thr Met Gln Leu Leu Gln Gln Gln
                165                 170                 175

Gln Gln Gln Gln Gln Gln Gln Gln Gln Gln Gln Gln Gln Gln Gln Gln
            180                 185                 190

Gln Gln Gln Glu Val Ile Ser Glu Gly Ser Ser Ser Val Arg Ala Arg
        195                 200                 205

Glu Ala Thr Gly Ala Pro Ser Ser Ser Lys Asp Ser Tyr Leu Gly Gly
    210                 215                 220

Asn Ser Thr Ile Ser Asp Ser Ala Lys Glu Leu Cys Lys Ala Val Ser
225                 230                 235                 240

Val Ser Met Gly Leu Gly Val Glu Ala Leu Glu His Leu Ser Pro Gly
                245                 250                 255

Glu Gln Leu Arg Gly Asp Cys Met Tyr Ala Ser Leu Leu Gly Gly Pro
            260                 265                 270

Pro Ala Val Arg Pro Thr Pro Cys Ala Pro Leu Ala Glu Cys Lys Gly
        275                 280                 285

Leu Ser Leu Asp Glu Gly Pro Gly Lys Gly Thr Glu Glu Thr Ala Glu
    290                 295                 300

Tyr Ser Ser Phe Lys Gly Gly Tyr Ala Lys Gly Leu Glu Gly Glu Ser
305                 310                 315                 320

Leu Gly Cys Ser Gly Ser Ser Glu Ala Gly Ser Ser Gly Thr Leu Glu
```

-continued

```
                325                 330                 335
Ile Pro Ser Ser Leu Ser Leu Tyr Lys Ser Gly Ala Val Asp Glu Ala
                340                 345                 350
Ala Ala Tyr Gln Asn Arg Asp Tyr Tyr Asn Phe Pro Leu Ala Leu Ser
                355                 360                 365
Gly Pro Pro His Pro Pro Pro Thr His Pro His Ala Arg Ile Lys
        370                 375                 380
Leu Glu Asn Pro Ser Asp Tyr Gly Ser Ala Trp Ala Ala Ala Ala
385                 390                 395                 400
Gln Cys Arg Tyr Gly Asp Leu Ala Ser Leu His Gly Gly Ser Val Ala
                405                 410                 415
Gly Pro Ser Thr Gly Ser Pro Ala Thr Ala Ser Ser Trp His
                420                 425                 430
Thr Leu Phe Thr Ala Glu Glu Gly Gln Leu Tyr Gly Pro Gly Gly Gly
                435                 440                 445
Gly Gly Ser Ser Pro Ser Asp Ala Gly Pro Val Ala Pro Tyr Gly
        450                 455                 460
Tyr Thr Arg Pro Pro Gln Gly Leu Ala Ser Gln Glu Gly Asp Phe Ser
465                 470                 475                 480
Ala Ser Glu Val Trp Tyr Pro Gly Gly Val Asn Arg Val Pro Tyr
                485                 490                 495
Pro Ser Pro Ser Cys Val Lys Ser Glu Met Gly Pro Trp Met Glu Asn
        500                 505                 510
Tyr Ser Gly Pro Tyr Gly Asp Met Arg Leu Asp Ser Thr Arg Asp His
        515                 520                 525
Val Leu Pro Ile Asp Tyr Tyr Phe Pro Pro Gln Lys Thr Cys Leu Ile
        530                 535                 540
Cys Gly Asp Glu Ala Ser Gly Cys His Tyr Gly Ala Leu Thr Cys Gly
545                 550                 555                 560
Ser Cys Lys Val Phe Phe Lys Arg Ala Ala Glu Gly Lys Gln Lys Tyr
                565                 570                 575
Leu Cys Ala Ser Arg Asn Asp Cys Thr Ile Asp Lys Phe Arg Arg Lys
                580                 585                 590
Asn Cys Pro Ser Cys Arg Leu Arg Lys Cys Tyr Glu Ala Gly Met Thr
        595                 600                 605
Leu Gly Ala Arg Lys Leu Lys Lys Leu Gly Asn Leu Lys Leu Gln Glu
        610                 615                 620
Glu Gly Glu Asn Ser Ser Ala Gly Ser Pro Thr Glu Asp Pro Ser Gln
625                 630                 635                 640
Lys Met Thr Val Ser His Ile Glu Gly Tyr Glu Cys Gln Pro Ile Phe
                645                 650                 655
Leu Asn Val Leu Glu Ala Ile Glu Pro Gly Val Val Cys Ala Gly His
                660                 665                 670
Asp Asn Asn Gln Pro Asp Ser Phe Ala Ala Leu Leu Ser Ser Leu Asn
                675                 680                 685
Glu Leu Gly Glu Arg Gln Leu Val His Val Val Lys Trp Ala Lys Ala
        690                 695                 700
Leu Pro Gly Phe Arg Asn Leu His Val Asp Asp Gln Met Ala Val Ile
705                 710                 715                 720
Gln Tyr Ser Trp Met Gly Leu Met Val Phe Ala Met Gly Trp Arg Ser
                725                 730                 735
Phe Thr Asn Val Asn Ser Arg Met Leu Tyr Phe Ala Pro Asp Leu Val
                740                 745                 750
```

-continued

```
Phe Asn Glu Tyr Arg Met His Lys Ser Arg Met Tyr Ser Gln Cys Val
            755                 760                 765

Arg Met Arg His Leu Ser Gln Glu Phe Gly Trp Leu Gln Ile Thr Pro
770                 775                 780

Gln Glu Phe Leu Cys Met Lys Ala Leu Leu Leu Phe Ser Ile Ile Pro
785                 790                 795                 800

Val Asp Gly Leu Lys Asn Gln Lys Phe Phe Asp Glu Leu Arg Met Asn
                805                 810                 815

Tyr Ile Lys Glu Leu Asp Arg Ile Ile Ala Cys Lys Arg Lys Asn Pro
            820                 825                 830

Thr Ser Cys Ser Arg Arg Phe Tyr Gln Leu Thr Lys Leu Leu Asp Ser
        835                 840                 845

Val Gln Pro Ile Ala Arg Glu Leu His Gln Phe Thr Phe Asp Leu Leu
    850                 855                 860

Ile Lys Ser His Met Val Ser Val Asp Phe Pro Glu Met Met Ala Glu
865                 870                 875                 880

Ile Ile Ser Val Gln Val Pro Lys Ile Leu Ser Gly Lys Val Lys Pro
                885                 890                 895

Ile Tyr Phe His Thr Gln
            900

<210> SEQ ID NO 7
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (4)..(4)
<223> OTHER INFORMATION: n is a or g

<400> SEQUENCE: 7 gccnccatgg                                                          10

<210> SEQ ID NO 8
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X can be any amino acid
<220> FEATURE:
<221> NAME/KEY: MISC_FEATURE
<222> LOCATION: (2)..(2)
<223> OTHER INFORMATION: X is Leu or Met
<220> FEATURE:
<221> NAME/KEY: MISC_FEATURE
<222> LOCATION: (3)..(5)
<223> OTHER INFORMATION: X can be any amino acid
<220> FEATURE:
<221> NAME/KEY: MISC_FEATURE
<222> LOCATION: (7)..(8)
<223> OTHER INFORMATION: X can be any amino acid
<220> FEATURE:
<221> NAME/KEY: MISC_FEATURE
<222> LOCATION: (9)..(9)
<223> OTHER INFORMATION: X is Val or Leu

<400> SEQUENCE: 8

Xaa Xaa Xaa Xaa Xaa Val Xaa Xaa Xaa
1               5
```

<210> SEQ ID NO 9
<211> LENGTH: 9
<212> TYPE: PRT
<213> ORGANISM: Artificial
<220> FEATURE:
<223> OTHER INFORMATION: synthetic peptide

<400> SEQUENCE: 9

Leu Leu Leu Phe Ser Ile Ile Pro Val
1               5

<210> SEQ ID NO 10
<211> LENGTH: 10
<212> TYPE: PRT
<213> ORGANISM: Artificial
<220> FEATURE:
<223> OTHER INFORMATION: synthetic peptide

<400> SEQUENCE: 10

Arg Met Leu Tyr Phe Ala Pro Asp Leu Val
1               5                   10

<210> SEQ ID NO 11
<211> LENGTH: 9
<212> TYPE: PRT
<213> ORGANISM: Artificial
<220> FEATURE:
<223> OTHER INFORMATION: synthetic peptide

<400> SEQUENCE: 11

Phe Leu Cys Met Lys Ala Leu Leu Leu
1               5

<210> SEQ ID NO 12
<211> LENGTH: 9
<212> TYPE: PRT
<213> ORGANISM: Artificial
<220> FEATURE:
<223> OTHER INFORMATION: synthetic peptide

<400> SEQUENCE: 12

Gln Leu Thr Lys Leu Leu Asp Ser Val
1               5

<210> SEQ ID NO 13
<211> LENGTH: 9
<212> TYPE: PRT
<213> ORGANISM: Artificial
<220> FEATURE:
<223> OTHER INFORMATION: synthetic peptide

<400> SEQUENCE: 13

Val Leu Glu Ala Ile Glu Pro Gly Val
1               5

<210> SEQ ID NO 14
<211> LENGTH: 9
<212> TYPE: PRT
<213> ORGANISM: Artificial
<220> FEATURE:
<223> OTHER INFORMATION: synthetic peptide

<400> SEQUENCE: 14

Ala Leu Leu Ser Ser Leu Asn Glu Leu
1               5

```
<210> SEQ ID NO 15
<211> LENGTH: 10
<212> TYPE: PRT
<213> ORGANISM: Artificial
<220> FEATURE:
<223> OTHER INFORMATION: synthetic peptide

<400> SEQUENCE: 15

Leu Gly Glu Arg Gln Leu Val His Val Val
1               5                   10

<210> SEQ ID NO 16
<211> LENGTH: 9
<212> TYPE: PRT
<213> ORGANISM: Artificial
<220> FEATURE:
<223> OTHER INFORMATION: synthetic peptide

<400> SEQUENCE: 16

Trp Met Gly Leu Met Val Phe Ala Met
1               5

<210> SEQ ID NO 17
<211> LENGTH: 9
<212> TYPE: PRT
<213> ORGANISM: Artificial
<220> FEATURE:
<223> OTHER INFORMATION: synthetic peptide

<400> SEQUENCE: 17

Phe Ser Ile Ile Pro Val Asp Gly Leu
1               5

<210> SEQ ID NO 18
<211> LENGTH: 9
<212> TYPE: PRT
<213> ORGANISM: Artificial
<220> FEATURE:
<223> OTHER INFORMATION: synthetic peptide

<400> SEQUENCE: 18

Lys Leu Leu Asp Ser Val Gln Pro Ile
1               5

<210> SEQ ID NO 19
<211> LENGTH: 9
<212> TYPE: PRT
<213> ORGANISM: Artificial
<220> FEATURE:
<223> OTHER INFORMATION: synthetic peptide

<400> SEQUENCE: 19

Gly Ile Leu Gly Phe Val Phe Thr Leu
1               5
```